(12) United States Patent
Melker et al.

(10) Patent No.: US 9,950,112 B2
(45) Date of Patent: Apr. 24, 2018

(54) INTELLIGENT DRUG AND/OR FLUID DELIVERY SYSTEM TO OPTIMIZING MEDICAL TREATMENT OR THERAPY USING PHARMACODYNAMIC AND/OR PHARAMACOKINETIC DATA

(75) Inventors: Richard J. Melker, Gainesville, FL (US); Donn M. Dennis, Gainesville, FL (US); Jeremy Melker, Gainesville, FL (US); Mark Rice, Jacksonville, FL (US); Robert Hurley, Gainesville, FL (US)

(73) Assignees: University of Florida Research Foundation, Incorporated, Gainesville, FL (US); Xhale, Inc., Gainesville, FL (US)

( * ) Notice: Subject to any disclaimer, the term of this patent is extended or adjusted under 35 U.S.C. 154(b) by 0 days.

(21) Appl. No.: 13/817,165

(22) PCT Filed: Aug. 17, 2011

(86) PCT No.: PCT/US2011/048083
§ 371 (c)(1),
(2), (4) Date: Apr. 29, 2013

(87) PCT Pub. No.: WO2012/024401
PCT Pub. Date: Feb. 23, 2012

(65) Prior Publication Data
US 2013/0296823 A1 Nov. 7, 2013

Related U.S. Application Data

(60) Provisional application No. 61/374,583, filed on Aug. 17, 2010.

(51) Int. Cl.
*A61M 31/00* (2006.01)
*A61M 5/172* (2006.01)
(Continued)

(52) U.S. Cl.
CPC .......... *A61M 5/1723* (2013.01); *A61M 5/142* (2013.01); *A61M 5/168* (2013.01);
(Continued)

(58) Field of Classification Search
CPC .... A61M 5/14; A61M 5/142; A61M 5/14244; A61M 5/168; A61M 5/172;
(Continued)

(56) References Cited

U.S. PATENT DOCUMENTS 5,025,791 A * 6/1991 Niwa ................. A61B 5/14552
600/324
5,063,938 A 11/1991 Beck et al.
(Continued)

FOREIGN PATENT DOCUMENTS

JP 05-124592 5/1993
JP 63-290542 11/1998
(Continued)

OTHER PUBLICATIONS

Statutory Invention Registration No. H1039, Tripp et al., Apr. 7, 1992.
(Continued)

*Primary Examiner* — Kevin C Sirmons
*Assistant Examiner* — Deanna K Hall

(57) ABSTRACT

A pharmacodynamic (PD), pharmacokinetic (PK), or both and PK guided infusion device, system and method optimizes the safety and efficacy of various forms of treatment or therapy (e.g., drug and/or fluid) in a variety of health-care and other settings.

12 Claims, 22 Drawing Sheets

(51) Int. Cl.
*A61M 5/142* (2006.01)
*A61M 5/168* (2006.01)
*A61M 5/315* (2006.01)
*G06Q 50/22* (2018.01)
*G06F 19/00* (2018.01)

(52) U.S. Cl.
CPC ........ *A61M 5/16854* (2013.01); *A61M 5/172* (2013.01); *A61M 5/31511* (2013.01); *G06Q 50/22* (2013.01); *G06F 19/3468* (2013.01)

(58) Field of Classification Search
CPC ...... A61M 5/1723; A61M 2005/14208; A61M 2005/14272; A61M 2005/1726; A61M 15/08; A61M 15/085; A61M 2005/14264; A61B 5/02416; G06F 19/3468
USPC ..... 604/131, 246, 500, 503, 504, 505, 890.1
See application file for complete search history.

(56) References Cited

U.S. PATENT DOCUMENTS

| | | | |
|---|---|---|---|
| 5,213,099 | A | 5/1993 | Tripp, Jr. |
| 5,275,159 | A | 1/1994 | Griebel |
| 5,278,627 | A | 1/1994 | Aoyagi et al. |
| 5,293,874 | A | 3/1994 | Takahashi et al. |
| 5,337,743 | A | 8/1994 | Repperger et al. |
| 5,396,893 | A | 3/1995 | Oberg et al. |
| 5,490,505 | A | 2/1996 | Diab et al. |
| 5,713,923 | A * | 2/1998 | Ward .............. A61M 5/14276 128/899 |
| 5,779,631 | A | 7/1998 | Chance |
| 5,817,010 | A | 10/1998 | Hibl |
| 6,081,735 | A | 6/2000 | Diab et al. |
| 6,157,850 | A | 12/2000 | Diab et al. |
| 6,165,151 | A | 12/2000 | Weiner |
| 6,263,223 | B1 | 7/2001 | Shepherd et al. |
| RE38,476 | E | 3/2004 | Diab et al. |
| 6,706,007 | B2 | 3/2004 | Gelfand et al. |
| 6,869,402 | B2 * | 3/2005 | Arnold .......................... 600/500 |
| 6,909,912 | B2 | 6/2005 | Melker |
| 6,959,708 | B1 * | 11/2005 | Rasor .................... A61H 33/14 128/200.24 |
| 6,976,963 | B2 | 12/2005 | Clift |
| 7,169,110 | B2 | 1/2007 | Lee et al. |
| 7,171,251 | B2 | 1/2007 | Sarussi et al. |
| 7,569,030 | B2 | 8/2009 | Lebel et al. |
| 8,161,971 | B2 | 4/2012 | Jaffe et al. |
| 8,182,443 | B1 | 5/2012 | Kiani |
| 8,695,591 | B2 | 4/2014 | Olson et al. |
| 2002/0028990 | A1 | 3/2002 | Shepherd et al. |
| 2002/0128544 | A1 | 9/2002 | Diab et al. |
| 2003/0036744 | A1 * | 2/2003 | Struys et al. ................. 604/503 |
| 2003/0051737 | A1 * | 3/2003 | Hickle ................ A61M 5/1723 128/898 |
| 2003/0236452 | A1 | 12/2003 | Melker et al. |
| 2004/0204636 | A1 | 10/2004 | Diab et al. |
| 2004/0236196 | A1 | 11/2004 | Diab et al. |
| 2007/0032732 | A1 | 2/2007 | Shelley et al. |
| 2007/0088334 | A1 * | 4/2007 | Hillis .................. A61B 5/0002 604/891.1 |
| 2009/0259114 | A1 | 10/2009 | Johnson et al. |
| 2010/0312075 | A1 | 12/2010 | McGonigle et al. |
| 2011/0270048 | A1 | 11/2011 | Addison et al. |
| 2013/0261468 | A1 | 10/2013 | Semler et al. |

FOREIGN PATENT DOCUMENTS

| | | |
|---|---|---|
| JP | 2001-204699 | 7/2001 |
| JP | 2003-024287 | 1/2003 |

OTHER PUBLICATIONS

Rusch et al., Signal processing methods for pulse oximetry, Computers in Biology and Medicine, vol. 26, No. 2, Mar. 1, 1996, pp. 143-159.
Hertzman, A.B. et al., Distinction between Arterial, Venous and Flow Components in Photoelectric Plethysmography in Man, Amer. Jour. Physiol., 130, 177 (1940).
Shelley, K.H., "Photoplethysmography: Beyond the Calculation of Arterial Oxygen Saturation and Heart Rate," Anesthesia & Analgesia, vol. 105, No. 6, Dec. 2007.
Allen, J., "Photoplethysmography and its application in clinical physiological measurement," Physiol. Meas. 28 (2007) R1-R39.
Ahlstrom, et al., "A Respiration Monitor Based on Electrocardiographic and Photoplethysmographic Sensor Fusion", Proceedings of the 26th Annual International Conference of the IEEE EMBS San Francisco, CA, USA • Sep. 1-5, 2004.
Johansson, A., "Neural Network for Photoplethysmographic Respiratory Rate Monitoring", Special Section on Bio-Optics, Med. Biol. Eng. Comput. 2003, 41.
Johansson, et al., "Estimation of Respiratory Volumes from the Photoplethysmographic Signal, Part I: Experimental Results", Med. Biol. Eng. Comput, 1999, 37.
Johansson, et al., Estimation of Respiratory Volumes from the Photoplethysmographic Signal, Part 2: a model study, Med. Biol. Eng. Comput, 1999, 37.
Leonard, et al., "Wavelet Analysis of Pulse Oximeter Waveform Permits Identification of Unwell Children", Emerg. Med. J., 2004.
Leonard, et al., "An Algorithm for the Detection of Individual Breaths from the Pulse Oximeter Waveform", Journal of Clinical Monitoring and Computing, 2004.
Nakajima, et al., "Monitoring of Heart and Respiratory Rates by Photoplethysmography Using a Digital Filtering Technique", Med. Eng. Phys. vol. 18, No. 5, 1996.
Nilsson, et al., "Macrocirculation is not the Sole Determinant of Respiratory Induced Variations in the Reflection Mode Photoplethysmographic Signal", Inst of Physics Publishing 24, 2003.
van Oostrom, et al., "Comparative Testing of Pulse Oximeter Probes", Anesth Analg, 2004.

* cited by examiner

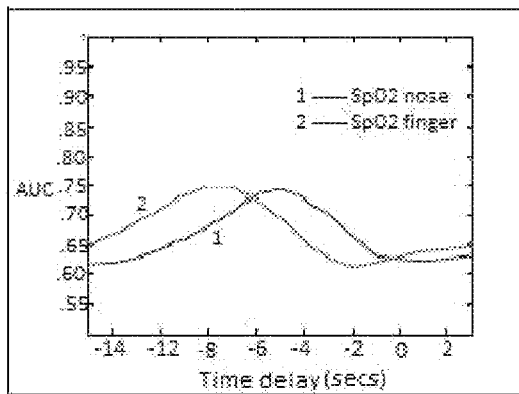 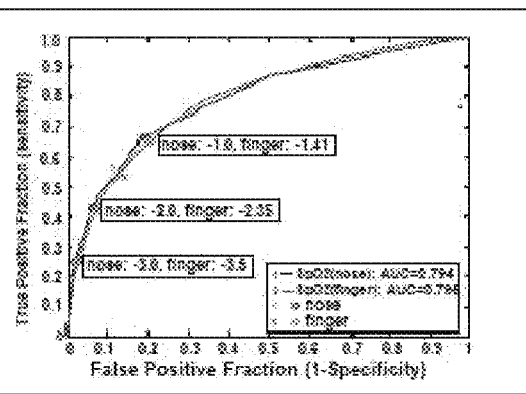
Figure 10(a)                    Figure 10(b)

INTELLIGENT DRUG AND/OR FLUID DELIVERY SYSTEM TO OPTIMIZING MEDICAL TREATMENT OR THERAPY USING PHARMACODYNAMIC AND/OR PHARAMACOKINETIC DATA

CROSS-REFERENCE TO RELATED APPLICATIONS

This application is the 35 U.S.C. § 371 national stage of, and claims priority to and the benefit of, PCT application PCT/U.S. 2011/048083, filed Aug. 17, 2011, which claims priority to and the benefit of U.S. Application No. 61/374,583, filed 17 Aug. 2010, the disclosure of each of which is hereby incorporated by reference in their entirety.

FIELD OF THE INVENTION

A pharmacodynamic (PD), pharmacokinetic (PK), or both PD and PK guided infusion device, system and method optimizes the safety and efficacy of various forms of treatment or therapy (e.g., drug and/or fluid) in a variety of health-care and other settings.

BACKGROUND OF THE INVENTION

In a number of scenarios, it is possible to safely infuse subjects with pharmaceutically active agents or fluids. In other scenarios, for example where a subject is to be infused with an opioid, there remains substantial danger to the subject, unless they are closely monitored, and, even then, in the absence of the safety features provided by the present device, system and method, substantial risk remains. The present invention, therefore, provides a solution to this long-felt need.

Conventional monitoring for respiratory depression in the hospital setting involves monitoring end tidal carbon-dioxide (ETCO2). However, ETCO2 is impractical in many scenarios. For example, it is difficult to measure in ambulatory patients (non-intubated patients). It is also costly, and the relevant equipment is cumbersome. The ability to directly monitor the pharmacodynamic (PD) effects of all of the factors that may contribute to hypopnea and/or apnea is far more valuable, for example, than knowing a single physiologic measurement, such as the ETCO2. Knowing the combined effects of $CO_2$, hypoxemia, opioids, other drugs, and physiologic state of a patient would provide much more valuable information for the patient's safety. Trending of various parameters would also be highly valuable, not only for closed-loop systems, but also for improved monitoring of patients in a hospital setting.

The present inventors have identified a number of existing technologies which may be adapted, as disclosed herein below in the detailed disclosure of the invention, for the particular purposes to be achieved by practice of the present invention. Thus, references to such technologies herein, and the documents in which those technologies are described, are to be considered as having been fully set forth.

For example, pending published US patent application, US2006/0241506 (METHOD AND APPARATUS FOR DIAGNOSING RESPIRATORY DISORDERS AND DETERMINING THE DEGREE OF EXACERBATIONS), hereafter "the '506 publication", involves the identification of peaks and troughs in plethysmograph signals, preferably acquired from a central site location of a subject, such as the nasal ala(e), identifying midpoints or minima between peaks and troughs, and using an interpolated line to represent venous impedance, permits extracting venous impedance and capacitance to thereby obtain an arterial component signal, thereby facilitating detection of an air obstruction event (such as apnea). As disclosed further herein below, such a system may be integrated into the present system, method, and device for enhanced safety in providing certain types of treatment or therapy in particular contexts. In particular, for example, in providing opioid therapy via a closed loop system, integration of such technology into an infusion device of this invention provides enhanced safety controls.

Likewise, with respect to published US patent application US2010/0192952, herein incorporated by reference, the present invention disclosure provides significant new applications and enhancements to the devices and methods disclosed therein. US2010/0192952 discloses certain pulse oximeter/plethysmography probes designed for securement to the nose, in a stand-alone form or incorporated into a mask of an air pilot or fire-fighter, pulse oximeter/plethysmography probes designed for securement to the pre-auricular portion of the a subject's ear, to the ear canal of a subject's ear, to the post-auricular portion of the subject's ear, or to the cheek of a subject's face. All of these designs are incorporated by reference into this disclosure, with the key modifications of these probes as described herein below, and the key modifications to the methods and systems disclosed herein which facilitate the safe, effective and efficient open- or closed-loop delivery of appropriate medications to the subject, dependent on the analysis of PD and/or PK signals obtained from the subject in either civilian or military contexts. The modifications and enhancement disclosed herein are likewise applicable to the context's disclosed in the US2010/0192952 publication, i.e. to prevent Gravity-induced Loss of Consciousness (GLOC) or Almost Loss of Consciousness (ALOC), as well as, for example, in the context of the fire-fighter. The key enhancements disclosed herein for this purpose include either an integrated or separately housed infusion system as well as enhancements achieved by coupling PPG signal acquisition and processing to nasal pressure signal acquisition and processing. In the contexts of GLOC and ALOC, for example, the present invention provides the option not only of altering the G-force induced loss or almost loss of consciousness, by setting off an alarm or interfacing with an aircraft's onboard computer, but to also, or instead, provide the option pharmacologic intervention, e.g. by detection of GLOC or ALOC and infusing the subject with an appropriate dose, for example, of glucose, epinephrine, oxygen or the like, or combinations thereof, calculated to avert the potentially catastrophic sequelae of a loss of consciousness in these circumstances.

Similarly, the technology described in Diab U.S. Pat. No. 6,157,850 (hereafter the '850 patent) provides, in particular with respect to blood oximetry measurements, methods, systems, algorithms and apparatuses to extract meaningful physiological information. Such a system may be integrated into the present method, device, system, to enhance safety by providing relevant pharmacodynamic (PD), pharmacokinetic (PK), or both PD and PK guided infusion in particular therapeutic contexts.

U.S. Pat. No. 7,569,030 and related Medtronic MiniMed patents (see, e.g. U.S. Pat. No. 6,827,702, and U.S. Pat. No. 6,740,972) describes a system for delivery of insulin for control of physiological glucose concentration. In these patents, however, there is very little disclosure about the "sensing device for sensing a biological state" element even for a closed loop system for delivery of insulin. The only sensing device identified is one for measuring glucose concentration. The main thrust of these patents is a system for setting safety limits for the amount of insulin provided by an infusion pump, and the ability for the user to over-ride certain limits to simulate, for example, the body's "leading insulin secretion reflex". Other over-rides, to address medications or activity states (sleep, stress, etc), forms a central part of the disclosure. Methods for calculating delivery rates of an infusion formulation of insulin in response to a sensed glucose concentration are disclosed.

The need for dynamic modelling to control opioid administration has been recognized. See, for example, Mitsis et al., *J Appl Physiol.* 2009 April; 106(4):1038-49, "The effect of remifentanil on respiratory variability, evaluated with dynamic modelling", (hereafter, "Mitsis et al.) which noted that opioid drugs disrupt signalling in the brain stem respiratory network affecting respiratory rhythm. Mitsis et al., evaluated the influence of a steady-state infusion of a model opioid, remifentanil, on respiratory variability during spontaneous respiration using dynamic linear and nonlinear models to examine the effects of remifentanil on both directions of the ventilatory loop, i.e., on the influence of natural variations in end-tidal carbon dioxide $PET_{CO2}$ on ventilatory variability, (which was assessed by tidal volume ($V_T$) and breath-to-breath ventilation i.e., the ratio of tidal volume over total breath time $V_T$/Ttot), and vice versa. Breath-by-breath recordings of expired $CO_2$ and respiration were made during a target-controlled infusion of remifentanil for 15 min at estimated effect site (i.e., brain tissue) concentrations of 0, 0.7, 1.1, and 1.5 ng/ml, respectively. They found that Remifentanil caused a profound increase in the duration of expiration. The obtained models revealed a decrease in the strength of the dynamic effect of $PET_{CO2}$ variability on $V_T$ (the "controller" part of the ventilatory loop) and a more pronounced increase in the effect of $V_T$ variability on $PET_{CO2}$ (the "plant" part of the loop). Nonlinear models explained these dynamic interrelationships better than linear models. The described approach allows detailed investigation of drug effects in the resting state at the systems level using noninvasive and minimally perturbing experimental protocols, which can closely represent real-life clinical situations.

By contrast, the present invention involves using physiological signals, software algorithms and infusion devices (e.g. with a subcutaneous catheter, implanted device and, in preferred embodiments, intranasal delivery, e.g. delivery to the mucosa of the nasal septum, particularly at Kiesselbach's plexus [also known as "Little's area"] and/or the nasal mucosa of the turbinates for the safe delivery of drugs which could potentially cause hypopnea, apnea and death if given in excess quantities. Since no single dose is appropriate for all individuals, and due to other medications and/or underlying clinical conditions, dosing without physiologic monitoring as disclosed herein, is unsafe. Furthermore, in the particular context of military operations, the present invention provides a system, method and apparatus, herein referred to by the acronym "WARCARE™", (Warfighter Autonomous or Remotely Controlled Advanced Resuscitation Ensemble), in which operatives in combat situations are able to receive appropriate pharmacologic intervention at a much earlier stage than has previously been possible. By coupling the PD, PK or PD+PK measurement sensors and signals of the present invention with the processor of this invention, and which then controls delivery of appropriate fluids and/or drugs to the combatant, morbidity and mortality and potentially Post-traumatic Stress Disorder (PTSD) is substantially reduced.

In addition, by incorporating WARCARE into the existing global positioning system, GPS) carried by the warfighter, the present invention will allow the military to locate, triage, monitor, and optimally treat injured warfighters with drugs and/or fluids, either locally (e.g., Level 1 military care) or remotely (e.g., rescue helicopters, and/or Levels 2 through 5 military care, etc.).

SUMMARY OF THE INVENTION

The system of this invention involves linking an apparatus or series of apparatuses which can reliably and rapidly (i.e. in as close to real time as possible) measure relevant PD, PK, or both PD and PK parameters of a subject, process the relevant PD, PK or PD+PK measurements and, on that basis, control one or more infusion pumps for closed-loop or open-loop delivery of opioids and other drugs or fluids to a subject. Such linkage is typically via a control system which implements appropriate algorithms as described herein for interpreting the PD, PK and any other relevant data, to control the rate of infusion of a particular therapeutic agent to appropriate delivery sites in the subject, including, but not limited to, intravenously, intraperitoneally, intranasally (whether in the form of a fluid, a mist, an aerosol, and/or a non-aerosol fluid delivery system and whether including or not including pharmacologically active compounds), as appropriate in a given context. For intranasal delivery, the therapeutic agents could be stored in various locations of the system, including near (or in) the nose or at sites more distant from the nose (e.g., adjacent to ear or forehead).

By so doing, it is possible, for example, to safely deliver opioids and other drugs to hospice or other patients with chronic pain, or in environments where the effective management of acute pain with narcotics is required (e.g., post-operative pain relief in hospitals). By monitoring their respiration, for example by implementing a device or system such as that described in the '506 publication, the danger of over-medication is reduced or eliminated.

The system, method and device of this invention may be optimized for use in civilian inpatient, outpatient or in military contexts, as described in detail below.

Accordingly, it is an object of this invention to provide a medication and/or fluid delivery and control system, method and apparatus which includes at least one apparatus for measuring at least one relevant pharmacodynamic (PD) parameter or at least one pharmacokinetic (PK) parameter or both at least one PD and at least one PK parameter in a subject; an infusion device with a rate of infusion which is increased, decreased, or maintained at a given level of infusion based on the at least one PD, PK, or at least one PD and at least one PK parameter; and a controller for receiving the at least one PD, at least one PK or at least one PD and at least one PK parameters and, based on the relevant parameters and hardware and software (including algorithms appropriate to the particular subject, context and treatment modality), increasing, decreasing or maintaining the rate of infusion of the infusion device(s).

It is a further object of this invention that in such a system, method and apparatus, the medication delivery and control system may be a closed-loop or an open-loop system.

It is a further object of this invention to provide appropriate algorithms, guidance and considerations relevant to a wide array of subjects and treatment regimens so that the advantages of the present system may be widely implemented and used for the added safety of subjects.

It is a further object of this invention to provide a system, method and apparatus optimized as a WARCARE™ system for delivery of early treatment to military personnel in contexts where, heretofore, such treatment has not been possible.

Other objects and advantages of this invention will become apparent from a review of the entire disclosure herein and from the appended claims and their equivalents.

BRIEF DESCRIPTION OF THE DRAWINGS

FIG. 10 shows saturation differences between a PPG probe placed at a Central Source Site (CSS), in this case, a nasal alar site, as compared with a Peripheral Source/Sensing Site (PSS), in this case, a finger, showing, in (a) optimal time shifts between finger and alar saturation and in (b) ROC curve of event prediction using finger and alar saturations.

DETAILED DISCLOSURE OF THE PREFERRED EMBODIMENTS OF THE INVENTION

The Delivery System of this Invention

Figure 1:
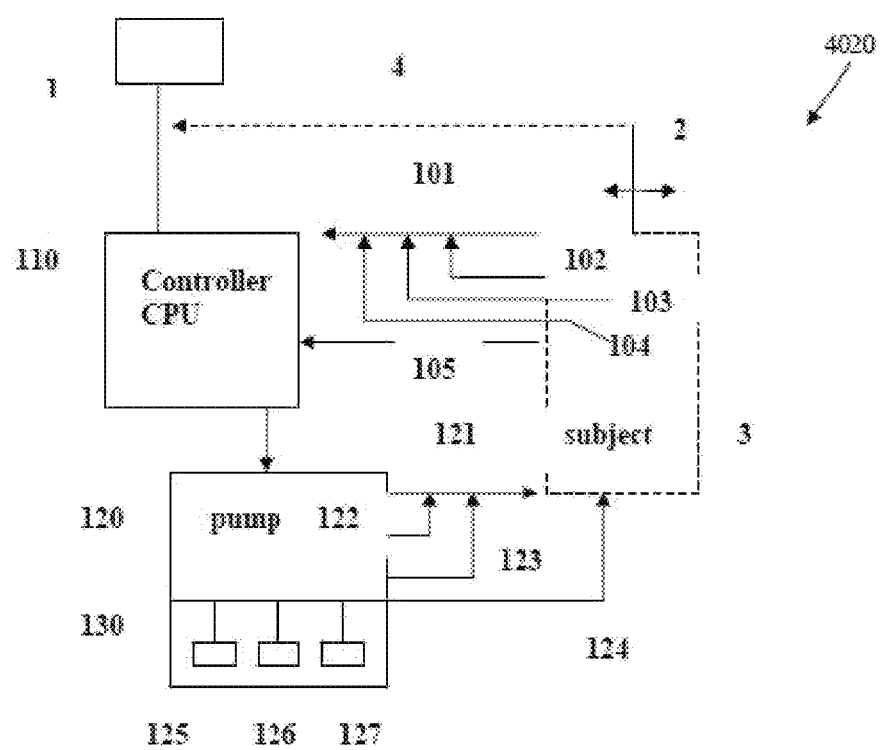
FIG. 1 provides a schematic representation of an apparatus of this invention, working as an integrated system to implement the method of this invention, whereby 1) PD parameters (biological responses, including but not limited to respiratory, hemodynamic, and movement responses, as defined above, to different blood concentrations of active pharmaceutical ingredients [APIs] such as opiates, propofol, etc) using PPG/ECG signals, are measured, 2) PK parameters (drug levels of APIs in blood such as opiates, propofol, etc. are measured using various biological matrices including but not limited to breath and blood), or 3) PD+PK parameters and other relevant signals are obtained from a subject and relayed to a controller which processes the incoming information from the subject to control at least one infusion pump which provides fluids and/or drugs to the subject at increased or decreased rates depending on the signals provided to it by the controller.

The present invention provides a means to control a fluid delivery device, such as an infusion pump, solenoids for release of pressurized gasses, aerosols and the like, or any other appropriate or equivalent fluid delivery device known in the art, for infusion of opioids, other drugs, fluids or any other composition which has a respiratory, hemodynamic or other pharmacologic effect in a subject. By coupling the infusion pump to a control system which receives and analyzes signals from one or more systems which measure appropriate pharmacodynamic (PD), pharmacokinetic (PK), or both PD and PK parameters of a subject, the infusion to the subject is then appropriately monitored and controlled by the control system.

As noted above, there are many known systems for measuring various PD and/or PK parameters in subjects. This invention provides a novel and unique system, method and apparatus for coupling known or novel (including those disclosed herein and which hereafter come to be known) PD and/or PK measurement systems to infusion apparatuses so that measurement of appropriate PD and/or PK parameters is conducted concurrent with or substantially concurrent with (i.e. there may be a slight delay of a few seconds or milliseconds between receipt of signals from the subject, processing of the signals and changes in the rate of infusion to the subject; delays in the signals are related to physiology and filtering—if, for example, the respiratory rate is 10-15 bpm, then detecting a change in the respiratory rate will take at least 10 seconds to ensure a single breath artifact does not indicate a false change in breath rate; therefore, it could take up to several seconds to detect a change in a slow physiologic signal—accordingly, the term "substantially concurrent with" is intended to mean a time of between about 0.1 millisecond and about 20 seconds, or between 1 millisecond and 15 seconds, or between 10 milliseconds and 10 seconds, or between 0.1 second and 1 second, as appropriate to the needs of a given situation) supply of medications, fluids or both. Based on instantaneous or substantially instantaneous (i.e. within a few seconds or milliseconds from the acquisition of signals from the subject) and/or trending of relevant PD and/or PK parameters, and based on appropriate algorithms (appropriate to a give subject, to a given subject type, to a given condition, to a given condition type), a control system is able to receive the PD and/or PK signals throughout an infusion or similar treatment process and to either increase, decrease or maintain the rate of infusion of one or more drugs and/or fluids to the subject. This substantially enhances the safety of such treatments for subjects in a wide variety of contexts (e.g. for hospital inpatients, for hospice patients, for subjects residing at home or alternative health care facilities, in old age homes or the like, and, e.g. in acute care, in chronic care, in the field for military personnel etc).

This invention provides an optimized device, system and method for medical therapy whereby pharmacodynamic (PD, e.g. respiratory and cardiovascular responses) and/or pharmacokinetic (PK, e.g. blood level, breath level—see, for example, U.S.20040081587—drug marker breath detection, U.S.20080059226—drug marker breath detection, US20080045825—glucose breath detection, and U.S. Pat. Nos. 7,104,963 and 6,981,947—propofol breath detection, all of which are herein incorporated by reference) measurements are utilized to guide infusion devices using closed and/or open control loop systems. By monitoring cardiorespiratory-based PD parameters, with or without measurement of PK parameters, the device, system and method of this invention non-invasively integrates a variety of factors, including but not limited to exogenous drug administration, attempts to resuscitate, and the like at the level of the cardiorespiratory system, in a manner that allows optimal regulation and titration of infusion rates of various drugs and fluid volumes. This technology substantially enhances such treatments by not only optimizing their efficiency, but also substantially enhancing the safety of such procedures, particularly in clinical settings where a manpower force multiplier is badly needed (e.g., war zones, hospices, hospitals, etc). It should be noted that by combining measurements of selected PD parameters, including but not limited to respiratory rate and consistency (e.g. low Respiratory Disturbance Indices, RDI's=the number of 10 second pauses per hour, with mild being considered to be 5-15 such events per hour, moderate being 15-30 and severe being anything above 30 per hour), cardiac output (e.g. by ECG measurement or plethysmography signal processing to obtain AC/DC components, as described in detail in, for example U.S.2010192952, herein incorporated by reference for this purpose), nasal pressure fluctuations (which permit accurate measures of breathing rate to be determined even when breathing via the mouth—nasal pressure waveform shapes also indicate characteristics of the breathing, such as the gradual increase in occlusion or resistance during exhalation or inhalation, increase in respiratory effort, and the like, all of which information is accessible and useable in various embodiments of this invention, as appropriate to a given situation), it is possible to obtain total "snapshots" of the physical status of the subject at any given time, summing up the influences of all external effects (e.g. gravity, low oxygen, high smoke or pollution, fluid or blood loss or other types of injury), and internal parameters (hypovolemia, anemia, any drugs operating in the metabolic pathways of the subject, etc), and provide appropriate pharmacologic intervention. It should be noted that while the term "snapshot" implies an instantaneous reading, "trends" and detection of changes in trends are also amenable to analysis and manipulation according to this invention. Trend analysis may be particularly important for plethysmography signal analysis, since plethysmography data requires calibration and therefore following trends provides clear benefits in this regard.

Coupling analysis if PD parameters, whether at particular instances or over periods of time to monitor trends, with PK parameter acquisition (e.g. by measurements of blood concentrations of pharmaceutically active compounds or their metabolites, or by measuring the concentrations of markers on the breath of the subject, whether such markers are the compounds themselves, surrogates for these compounds or metabolites thereof), permits a total picture for the subject to be accessed at any given time, and integrated into the pharmacologic response. Such responses, per one embodiment of this system, method and apparatus of this invention, is entirely autonomous and self-contained—all signal acquisition, processing and infusion responses are integrated into a system which the subject incorporates into their attire (whether as part of a helmet, belt, probes affixed to appropriate physiological aspects—nasal alae, ears, cheek, and whether PPG probes, nasal pressure probes, ECG probes or the like). Alternatively, or in addition, via appropriate telemetry, wired or wireless technology (whether using GPS signals, internet, 3G, 4G, infrared, ultrasound, or any other electromagnetic radiation means, now known or hereinafter developed), the system may communicate with and optionally be under the control of external analysis and control. This latter option provides for force-multipliers to come into operation, allowing a central person or teams of persons to analyse data relevant to one or multiple individuals and to over-ride autonomous operation and provide even more appropriate interventions then are possible under completely autonomous operation of the system, method or apparatus of this invention.

Drug Delivery Modes: Although the preferred embodiment of this invention includes one or more infusion devices, a number of other drug delivery modes, used alone or in combination, can be utilized with this invention. They include but are not limited to:

Continuous drug and fluid administration: Introduction of a medication (or fluid) into the body in a continuous (dosing rate may vary however) manner. Although in this scenario most applications would include the administration of intravenous drugs or fluids, it could also entail, for example, transdermal skin patches that continuously deliver drugs through the skin, subcutaneous, rectal, intraosseous and intranasal administration.

Intermittent drug administration: Introduction of a medication (or fluid) into the body in an intermittent manner. Examples here include but are not limited to intermittent dosing with oral, eye, intravenous, subcutaneous, intranasal, intraosseous or inhalational drugs.

The delivery of fluids and/or gasses may be via appropriate pumps, or, in a preferred embodiment, pressurized vessels containing appropriate fluids, drugs, nutrients (e.g. glucose) and the like, are released in pre-metered doses on actuation of a release mechanism (a valve, servo, septum or the like). Each time a particular pressurized vessel is instructed by the system to release a pre-metered dose, an appropriate dose is delivered to the subject. By sending multiple instructions, multiple doses may be applied to the subject to simulate almost continuous infusion until a reduce delivery signal or a cease delivery signal is applied to prevent further infusion of the particular agent or agents to the subject.

Site of Drug Administration: Using different types of drug (or fluid) delivery modes, a wide variety of drug administration sites exist, including but not limited to the following: intravascular (intravenous or intraarterial), subcutaneous, oral, intranasal, intraosseous, transdermal (e.g., iontophoretic or non-iontophoretic-based), intramuscular, intravaginal, sublingual, rectal, intraosseous, transocular (eye) or intraocular, intraotic, pulmonary or intrapulmonary (transtracheal, or via metered dose inhalers [MDIs]), epidural, intrathecal, neuraxial (central nerves, peripheral nerves), and intracerebral. In a particularly preferred embodiment, because of the high rate of bioavailability, absorption and low time for effect, delivery to the nasal epithelium is utilized. Delivery may be by application of a fluid, an aerosol, a non-aerosol, or the like, with or without permeability enhancing compounds.

Examples of Medical Therapies: Any medical therapy (e.g., drug and/or fluids) that modulates cardiorespiratory function (stimulates and/or depresses) in vivo, namely the respiratory centers in the brain and/or the cardiovascular system, can be controlled with the current invention in a manner that will substantially improve outcomes in terms of improved drug safety and efficacy, and reduced morbidity and mortality. In addition to the PD control of drug delivery described above, PK based strategies, used alone, or in combination with PD can be devised. Examples of medical therapies which can be controlled in this manner include:
Conscious sedation or general anesthesia
Pain relief
Attention Deficit Hyperactivity Disorder(ADHD)
Treatment of cardiovascular disorders, including trauma
Migraine headaches
Drug Treatments:
Narcotics (e.g., sufentanil, morphine, fentanyl, alfentanil, oxycodone, methadone, oxymorphone, Remifentanil),
Anesthetics and anesthetic adjuncts (e.g., inhalational anesthetics [sevoflurane, xenon, isoflurane, desflurane], intravenous anesthetic agents [propofol, ketamine, dexmedetomidine, benzodiazepines], and local anesthetics [lidocaine, bupivacaine, ropivacaine]).
ADHD treatment (e.g., short and long acting CNS stimulants including but not limited to methylphenidate, amphetamine, methamphetamine).
Migraine headaches (e.g., dehydroepiandrosterone [DHEA], lidocaine, serotonin receptor modulators, such as triptans)
Weight loss medications (e.g., phenteramine)
Cardiovascular drugs (e.g., dopamine, dobutamine, ephedrine, vasopressin, epinephrine, norepinephrine, beta and alpha receptor agonists and antagonists, phosphordiesterase inhibitors, etc.)
Non-Drug Treatments:
Fluids, including volume expanders, nutrients, e.g. glucose, given via the intravascular route, including intravenously, intraarterially and intraosseously
efficacy of cardiovascular assist devices (e.g., automated chest compressors, manual cardiopulmonary resuscitation, intraortic balloon pumps).

PD-Based Sensor Locations: Number—1) single (nasal ala; ear, finger; etc), and 2) multiple (e.g., nasal alae+finger; nasal ala+finger+toe); Location: central (e.g., ala, lip, cheek, tongue) versus peripheral (e.g., toe, finger, ear) photoplethysmograph (PPG) sensors.

Type of Sensors that Guide Therapy: PD (cardiorespiratory information): photoplethysmograph (PPG), capnograph (IR, etc), nasal pressure, nasal flow, electrocardiogram (ECG), chest wall impedance, any parameter measureable using polysomnography or combinations thereof; PK (drug blood levels) information: nanosensors for breath; others for other biological media, etc.; integrated sensors that integrate PD and PK information.

Basis of Control Loop: Pharmacodynamic-based, Pharmacokinetic-based, or a combination of the two.
1. Output of PD-based sensors: Numerical parameters indicating cardiorespiratory function, including but not limited to heart rate, respiratory rate, $ET_{CO2}$, blood oxygenation, respiratory effort (work of breathing [WOB]), pulse transit time (PTT), evidence of hypovolemia using process signaling of PPG signal with single or multiple probe approach that will provide the degree of respiratory-based variation in the PPG signal; deoxygenation index (DIB).
2. Output of PK-based sensors: Measurement of drug levels in various biological media (e.g., breath, saliva, skin, tears, sweat, blood, urine) to guide treatment.

Note: The PD and PK data used to control medical therapy uses computer unprocessed and/or processed data derived from the sensors. In addition, this invention claims the utility of regulatory drug therapy using open loop control systems, where the information does not regulate the drug output from an infusion device but rather informs a health care worker, family member, or the patient that his/her dose requires change or no change, and provides information on the well being of the patient during therapy.

Anatomical Location of Infusion Device: A. Internal—within the body (e.g., subcutaneous, intravascular, intracerebral, intraocular, intrathecal); B. External—Transdermal patches, rectal, vaginal, sublingual.

Care Environments: Hospitals, Hospices, Homes, Nursing Homes, Skilled Nursing Facilities, Surgery Centers, Military settings (war zones, hospitals, medevac settings and the like), aeronautical, outer space or subaquatic environments.

General Description of Single Point of Contact (SPOC) Diagnostic System of this invention and Signal Processing Algorithms and Procedures Relevant to Practicing this Invention:
Please see Appendix 1 to this disclosure, hereby incorporated here by reference for this purpose. As can be seen, the conclusion reached is that the SPOC system "appears to be robust to differences in patient population and performs well relative to other systems on the market. The system uses a unique combination of nasal pressure, saturation, and plethysmography parameters and each of the 4 parameters contributes unique information that is utilized by the system. Although there were a few outliers in the validation set that produced a lower than expected correlation with RDI, these outliers are largely caused by two factors: (1) the difference between sleep time and valid data time (our surrogate for sleep), and (2) our focus on correctly discriminating mild and moderate patients. The largest outliers were limited to the very high RDI patients (RDI>80) and the RDI correlation for patients with RDI<80 was 0.96. Even with the sleep-time induced underestimates, the White/Westbrook diagnostic agreement was 93%. With compensation for this sleep time disparity, the diagnostic agreement was 100%."

Thus, utilizing the details, methodology and analysis discussed in Appendix 1, those skilled in the art are enabled to reproduce the SPOC analysis and outputs relevant to both civilian and military applications outlined in further detail above and in the additional examples provided below. These outputs permit the selection of appropriate interventions using a closed loop system in which the PD parameters are continually monitored and pharmacologic closed-loop or open-loop interventions are initiated. Thus, as a result of determining that a subject as an unacceptably high RDI for example, whether in a sleep apnea context or in the context of a warfighter who is not breathing as they should, appropriate medication can be administered by the system, the impact of which is monitored by the subsequent PD parameters of the individual. This results in the system adapting the intervention to match the subsequent state of the subject, either by increasing, decreasing or ceasing the particular intervention. Of course, however, the parameters that may be monitored extend well beyond the RDI measurements to which the information in the Appendix is primarily directed.

EXAMPLES

While the foregoing disclosure generally describes this invention, the following examples are provided to further describe and enable this invention. It will be appreciated, however, that these examples and the specifics provided therein are non-limiting and those skilled in the art could vary or use equivalent methods, apparatuses and systems, without departing from the heart of the invention.

Example 1

In subjects receiving prescriptions for opioids and/or combinations of opioids with other medications, either prescribed or taken against medical advice (e.g. ethanol), which increase the potential for drug overdose/respiratory depression/arrhythmias (oxycodone, fentanyl TD, morphine ER, oxycontin, dextromethorphan in combination with others) for home use, adherence and well being are monitored using a cardiorespiratory-based PD sensor according to the invention.

For oral medication(s), the patient is provided with a small microprocessor/microcomputer that is worn on the belt (or over the ear similar to a hearing aid) and attaches (either directly or by communications such as Bluetooth) to a small sensor array which is attached at a single point of contact (SPOC) to one nasal ala. The SPOC array consists of one or more of the following: an extremely small pulse oximeter sensor (photodiodes [one or more LEDs] and a photodetector), a nasal pressure sensor, one of at least two ECG leads, a nasal flow sensor (thermistor or other). The SPOC is light weight and barely visible.

The SPOC array continuously monitors cardiorespiratory parameters such as ECG, SpO2, photoplethysmography (PPG) (from which respiratory rate, respiratory effort, arterial blood flow, venous capacitance and other parameters are derived), nasal pressure or flow (as a watchdog function for respiratory parameters derived from the PPG). The SPOC system optionally also includes an accelerometer to monitor the position of the patient.

When the patient is upright and moving, the microprocessor goes into a standby or sleep mode where it uses low power to monitor the accelerometer. If the patient reclines or motion decreases markedly, the microprocessor wakes-up and continuously monitors the patient.

The changes in brainstem function associated with respiratory depression from opioids is well documented. The association with multiple drugs and various disease states is more complicated, but since SPOC provides the microprocessor with a variety of physiologic signals, the algorithms access the TOTAL EFFECT of all factors on the cardiorespiratory systems.

In the instance where a patient begins to have diminished cognitive and/or brainstem function, the microprocessor determines, from the SPOC derived parameters, that the patient is beginning to have diminished responsiveness based on the characteristic changes. These are seen in the respiratory pattern, rate and depth of breathing as well as in the cardiac system, where loss of pulse rate variability is often seen. Additionally, the accelerometer determines that the patient's activity has decreased substantially, indicating that the patient is sleeping and/or suffering the effects of brainstem depression. Algorithms based on SPOC derived data determine the differences between normal sleep and respiratory/cerebral depression.

When the microprocessor determines the decreased activity and/or the SPOC derived parameters indicate respiratory depression, an alert function, such as alarms, and messages sent to care givers, family members and healthcare professional including EMS, are activated. This alert can be sent by conventional telephone modem, wirelessly, by cable or other means (such as satellite) to provide the necessary support for the patient.

Example 2

Optimal sedation in patients undergoing colonoscopies using a combined PK (e.g. using breath analysis used to measure blood levels of propofol)-, and PD (e.g., using cardiorespiratory-derived parameters from PPG)-based system to control of an infusor device is used to safely deliver IV propofol. A PK+PD-based propofol infusion system that provides drug effects on respiratory and cardiovascular systems is therefore enabled and is easily implemented by those skilled in the art in light of the teachings provided herein.

In the case of propofol, it would be ideal to have a drug delivery system that would guide intravenous (IV) infusion rates based on a closed loop control system using both PK (relationship between propofol dose and propofol blood concentration) and PD (relationship between propofol blood concentration and biological response, namely effects of propofol on cardiorespiratory function) inputs. When a drug such as propofol is given IV, the relationship between dose and pharmacological effect is interspersed by two important factors: PK (dose-concentration relationship) and PD (concentration-response relationship). In general, for most IV drugs, it appears that the variability between dose and pharmacological effect is approximately due to equal contributions from variabilities in PK and PD. However, this contribution can vary by drug (see below for propofol, where PK variability appears more important than PD variability). In general for controlling IV drug infusions, irrespective of PK versus PD contributions to variabilities in dose-response, it is preferable to guide drug dosing based on the biological effects of the drug, because it takes into account the multitude of factors that can alter PK and/or PD, and integrates them at the level of biological responsiveness, which in turn controls drug infusion rates, either in a closed loop (machine outputs automatically modifies drug infusion rates) or open loop (human takes system output and modifies drug infusion rate) configuration. In the case of propofol, during sedation where the subjects are breathing spontaneously, the cardiorespiratory effects of propofol at various levels of anesthesia are well known, and SPOC-derived parameters (see Example 1) are well suited to guide drug infusion rates. In contrast, during deeper levels of anesthesia where the patient may become apneic (not breathing spontaneously), due to general anesthesia or when sedative levels of anesthesia become too deep, many of the biological variables emanating from SPOC are lost and the closed-loop control mechanism will not be solely adequate to guide propofol infusion rates. In this scenario, using PK (determine blood levels of propofol using breath measurements) as opposed to PD, becomes important, because the anesthesia provider can use blood levels as an index of anesthetic depth in a given patient, particularly when they trend the blood levels of propofol with PD parameters when the patient was breathing spontaneously and/or when he/she become apneic. In this manner, PD and/or PK parameters are highly complementary management tools to guide drug infusion rates and to optimize drug safety and efficacy in most clinical scenarios that employ the use of propofol. The measurement of propofol levels in breath to estimate blood levels is an extension of what anesthesia providers currently use for volatile anesthetics (e.g., desflurane, isoflurane, sevoflurane, etc).

In this embodiment, it is technologically feasible to use breath levels of propofol to determine propofol PK in humans. Specifically, several independent groups around the world have conclusively demonstrated that propofol (the parent molecule that causes anesthesia, not a metabolite) appears in the exhaled breath of humans and that exhaled concentrations of propofol correlate to those found in the serum. The following table summarizes these findings:

| Instrument Used to Measure Breath Propofol | Correlation Coefficient (r2) | References |
|---|---|---|
| SAW | N/A | Melker, RJ et al, USPTO 7,104,963). 9-12-2006. |
| PTR-MS | N/A | Harrison GR et al, Real-time breath monitoring of propofol and its volatile metabolites during surgery using a novel mass spectrometric technique: a feasibility study. Br. J. Anaesth. 2003; 91: 797-9 |
| IMR-MS | 0.85-0.96 | Hornuss C et al, Real-time monitoring of propofol in expired air in humans undergoing total intravenous anesthesia. Anesthesiology 2007; 106: 665-74 |
| PTR-MS | "High" | Takita A et al, On-line monitoring of end-tidal propofol concentration in anesthetized patients. Anesthesiology 2007; 106: 659-64 |
| HS-SPME-GC-MS | 0.85 | Miekisch W et al, Assessment of propofol concentrations in human breath and blood by means of HS-SPME-GC-MS. Clin. Chim. Acta 2008; 395: 32-7 |
| MCC-IMS | 0.73 | Perl T et al, Determination of serum propofol concentrations by breath analysis using ion mobility spectrometry. Br. J. Anaesth. 2009; 103: 822-7 |
| HS-SPME-GC-MS | 0.83 | Gong Y et al, Investigation of Propofol Concentrations in Human Breath by Solid-phase Microextraction Gas Chromatography-Mass Spectrometry. J. Int. Med. Res. 2009; 37: 1465-71 |

Abbreviation Key:
Although this table includes only human data, a large amount of non-human data also confirms this relationship.
Abbreviations:
SAW; surface acoustic wave;
PTR-MS, proton transfer reaction-mass spectroscopy;
IMR-MS, ion-molecule reactions coupled with quadrupole mass spectrometry;
HS-SPME-GC-MS, headspace solid-phase microextraction gas chromatography-mass spectrometry;
MCC-IMS, mobility spectrometer coupled to a multicapillary column for pre-separation.

Propofol: Importance of PK Versus PD in Drug Response:

The biological effect of every drug is influenced by variability in PK (relationship between dose and concentration) and PD (relationship between concentration and effect). The relative contribution of PK and PD variability of propofol on clinically determined end-points has been studied (Minto et al, Using the time of maximum effect site concentration to combine pharmacokinetics and pharmacodynamics. Anesthesiology. 2003; 99: 324-33). The concentrations of drugs can be used to determine (or at least estimate) the effects of drugs such as isoflurane, valproic acid, vancomycin, gentamycin, cyclosporine, and others. Although the exact nature of the relative contributions of PK and PD are not well specified for most agents that undergo therapeutic drug monitoring, many clinicians still measure (and insurance companies pay for) their concentrations and integrate this data into overall patient care. However, perhaps the best example of drugs where blood (and breath) concentrations can be readily used to determine biological effects is volatile anesthetics in the anesthetic arena. For example, similar to minimum alveolar concentration (MAC) values for volatile anesthetics currently measured in the OR such as sevoflurane, propofol demonstrates a concentration-response curve to cause various biological effects. Although reproduced many times, the original work of Schafer and colleagues from the 1980s demonstrates the relationship between propofol concentration and unconsciousness in human surgical patients (Shafer A et al, Pharmacokinetics and pharmacodynamics of propofol infusions during general anesthesia. Anesthesiology. 1988; 69: 348-56). The EC50 values for awakening and orientation were remarkably similar (1.07±0.13 and 0.95±0.19 μg/ml, respectively), and were independent of patient age, sex, weight, liver function test results, or type of surgery (Shafer A et al, Anesthesiology, 1988; 69: 348-56). Awakening and orientation are important values to anesthesiologists in order to facilitate operating room turnover and efficiency.

Moreover, the blood concentration of propofol was used by several groups to demonstrate that BIS actually measures anesthetic depth. That is, propofol concentrations were used as the "gold standard" of anesthetic depth when developing the bispectral index (BIS) monitoring system. In these studies of human surgical patients, the blood concentration of propofol was compared to the BIS value at various planes of anesthesia measured by many sedation scores (Iselin-Chaves I A et al, Changes in the auditory evoked potentials and the bispectral index following propofol or propofol and alfentanil. Anesthesiology. 2000; 92: 1300-10; Doi M et al, Relationship between calculated blood concentration of propofol and electrophysiological variables during emergence from anaesthesia: comparison of bispectral index, spectral edge frequency, median frequency and auditory evoked potential index. Br. J. Anaesth. 1997; 78: 180-4). Clearly, propofol concentrations correspond to anesthetic depth as determined not only by clinical endpoints, but also by BIS measurement. Taken together, these results collectively indicate that variability in PK is a more important predictor of changes in the biological effects of propofol than variability in PD (i.e., blood levels of propofol in humans reliably translate to predictable anesthetic responses whereas doses of propofol do not reliably translate to predictable blood levels of propofol). This finding is consistent with the failure of a targeted control infusion (TCI) system for propofol (Diprifusor™), which was designed to give predictable blood levels based on population PK parameters, to function well clinically (Frölich M A et al, Precision and bias of target controlled propofol infusion for sedation. Br. J. Anaesth. 2005; 94:434-7). 12 In other words, due to variability in PK parameters among humans, the TCI systems did not accurately predict blood levels of propofol in humans, because it is based on global PK parameters. Therefore, by removing PK variability "out of the equation", a system that measures breath propofol (and hence blood levels) would accurately assess the PD (anesthetic effects) of this important and widely used IV anesthetic, and thus be valuable in the management of patients undergoing propofol anesthesia.

Embodiment of Close Loop Propofol System in Example 2:

In the setting of sedation using propofol, the patient is provided with a small sensor array which is attached at a single point of contact (SPOC) to one nasal ala and a custom designed breath mask to allow breath levels of propofol to be determined. A small microprocessor/microcomputer is placed near the head of the patient, either attached to the OR table/stretcher or a nearby IV pole. Communications between the SPOC and microprocessor will be via a direct connection or by wireless communications such as Bluetooth. The SPOC array consists of one or more of the following: a small pulse oximeter sensor (photodiodes [one or more LEDs] and a photodetector), a nasal pressure sensor, one of at least two ECG leads in the SPOC (or interfaced to ECG leads used by the conventional anesthesia monitoring system), a nasal flow sensor (thermistor or other). The SPOC is light weight. The breath levels of propofol will be measured using a sensor including but not limited to a surface acoustic waveform (SAW) technology, via either a side-stream analyzer or an in-line system attached to the breath mask. Measurements of the propofol will be gated to obtain end tidal samples according to the phase of ventilation using various respiratory parameters including but not limited to ETCO2, temperature, humidity and pressure. The SAW sensor output will be integrated into the SPOC-microprocessor system (either wirelessly or via direct connection) to provide near real-time measurements of propofol blood levels (via the SAW sensor) and the biological effects (via the SPOC system) of propofol. A weighted numerical scoring system, which takes into account the various PK and PD parameters, will be one method that is devised to control propofol infusion rates. Obviously, when apnea occurs, the propofol infusion will be guided by PK, whereas at lower levels of propofol anesthesia depth where spontaneous ventilation is present, PD will have a more important role. When the microprocessor determines the decreased activity and/or the SPOC derived parameters indicate respiratory depression, an alert function, such as alarms, and messages will be sent to the anesthesia provider as the system simultaneously modifies the infusion rate of propofol.

The SPOC array continuously monitors cardiorespiratory parameters such as ECG, SpO2, photoplethysmography (PPG) (from which respiratory rate, respiratory effort, arterial blood flow, venous capacitance and other parameters are derived), nasal pressure or flow (as a watchdog function for respiratory parameters derived from the PPG). The SPOC system optionally also includes an accelerometer to monitor the position of the patient during sedation and general anesthesia. When the patient is moving, the microprocessor notifies the anesthesia provider.

In summary, the cardiorespiratory changes caused by different concentrations of propofol on the cardiorespiratory centers of the brainstem are well documented. Because propofol has variable PK between humans and its PD effects can be markedly augmented by many factors including disease or the presence of other drugs (e.g., benzodiazepines, opioids), the use of SPOC to measure biological effects of propofol is desirable, because it takes into account and integrate all these factors at the level of propofol's effects on the cardiorespiratory systems. For example, if the anesthesia provider solely used propofol blood levels alone to guide propofol dosing, he/she may well overdose the patient, if midazolam (a benzodiazepine) and/or fentanyl (a potent narcotic) were administered, because they sensitive the brainstem to the respiratory effects of propofol but do not change the blood levels of this widely used IV anesthetic.

Example 3

Alcohol (e.g. ethanol) is detected (important during titration as well as chronic use) on breath during adherence testing for oxycontin. Subjects may be randomly called and requested to emplace the PD system on their nose, and/or to test for adherence, and/or to test for the presence of alcohol blood levels. A system used to monitor adherence to and/or to prevent diversion of oxycontin as well as automatically detect blood levels of ethanol (using breath) is incorporated into a PD-based system to measure the biological effect of oxycontin and any significant interaction with ethanol on cardiorespiratory function.

The diversion of prescription opioids for non-medical use is a national epidemic. In 2008 2.2 million Americans initiated nonmedical use of prescription opioids, and 1.24 million met DSM-IV criteria for opioid addiction (Substance Abuse and Mental Health Services Administration. (2009). Results from the 2008 National Survey on Drug Use and Health: National Findings (Office of Applied Studies, NSDUH Series H-36, HHS Publication No. SMA 09-4434). Rockville, MD. Unfortunately, opioids frequently cause mortality, because it suffers from a major PD interaction with ethanol. Specifically, ethanol markedly sensitises the cardiorespiratory centers of the brainstem to the depressant effects of opioids, frequently leading to apnea and death. This problem is not limited to opioids. There are at least 220 US approved drugs where specific warnings against ethanol intake are listed in the label. The potentially lethal interaction of ethanol with many drugs occurs almost exclusively at two levels: 1) PK: ethanol levels alter blood levels of active drug (e.g., abacavir), and/or 2) PD: ethanol alters the biological target sensitivity to the active drug but does not alter blood levels (e.g., opioid: Oxycontin [oxycodone]; benzodiazepine: Xanax [alprazolam]). Most significant interactions with ethanol occur with the latter mechanism.

In this embodiment, we (our patent references) are developing medication adherence systems that can monitor narcotic (opioid) adherence and prevent opioid diversion by analyzing "breathprints" of generally recognized as grass (GRAS) compounds, which are FDA approved compounds for use in foods (additives or natural). The sensor used to detect these unique chemical patterns in the breath, termed a miniature gas chromatograph-metallic oxide sensor (mGC-MOS), not only detects adherence to drugs, but also can be used to sensitively and specifically detect and quantitate ethanol in blood, even at very low concentrations. Thus, the use of the mGC-MOS has a dual benefit in this clinical scenario: 1) monitor adherence to opioids and prevent diversion, and 2) make opioid treatment safer, because it can be used to avoid the many PK and/or PD interactions with ethanol. This embodiment (assessing medication adherence along with regular or intermittent checks on blood ethanol levels using the breath) highlights it applicability to opioids (narcotics), but it is equally useful for many other drug classes with known PK/PD interactions with ethanol, including but not limited to: 1) alcoholism treatments (e.g., disulfuram), 2) antibiotics (e.g., isoniazid, rifampin, metronidazole), 3) anticoagulants (e.g., warfarin), 4) antidepressants (e.g., tricyclic antidepressants, selective serotonin reuptake inhibitors, SRNIs), 5) Antidiabetic medications (e.g., oral hypoglycaemic agents), 6) antihistamines (e.g., diphenhydramine), 7) antipsychotics (e.g., chlorpromazine), 8) antiseizure medications (e.g., phenyloin), 9) antiulcer medications (e.g., cimetidine), 10) cardiovascular medications (e.g., statins, beta blockers, nitroglycerin, hydralazine), 11) opioids (e.g., oxycodone, morphine, codeine, propoxyphene), 12) non-narcotic pain relievers (e.g., NSAIDs such as aspirin; non-NSAIDs such as acetaminophen), and 13) sedatives/hypnotics (e.g., benzodiazepines such as diazepam, alprazolam, lorazepam, flurazepam; barbiturates such as secobarbital, pentobarbital and phenobarbital).

Optimal safety and efficacy monitoring of a patient receiving oxycontin (during titration phase and chronic management) using PD-based safety monitoring to detect both opioid and opioid-ethanol interactions on cardiorespiratory function is achieved according to the method of the present invention, with medication adherence and ethanol monitoring, and with continuous (patient places SPOC on nasal alae with each oxycontin ingestion) or intermittent (patients places SPOC on nasal alae by random call request), as described above.

Example 4

Optimal pain therapy in patients suffering cancer or postop pain using PK (e.g. using breath analysis to measure blood levels of narcotic), PD (respiratory-derived parameters using PPG)-, or a combined PK/PD-guided control of an infusor device delivering IV narcotics (opioids). In light of the present disclosure, a PD-based narcotic infusion system that provides drug effects on respiratory and cardiovascular systems is enabled and easily implemented by those skilled in the art.

Example 5

Safety and efficacy monitoring of a chronic pain patient prescribed a 1 month supply of opioid (e.g., Oxycontin) using PD-based safety monitoring is achieved according to the method of the present invention, with or without medication adherence, and with or without ethanol monitoring, as described above.

Example 6

Safety and efficacy monitoring of a chronic pain patient given a transdermal fentanyl patch using PD-based safety monitoring (intermittent or continuous, linked to a monitoring station) is achieved according to the present invention, with or without medication adherence, and with or without ethanol monitoring, as described above.

Example 7

Optimal anesthesia using total intravenous anesthesia (TIVA) in patients undergoing procedures, both in civilian and military environments, using PK (e.g. breath analysis used to measure blood levels of anesthetic agents)-, PD (e.g., effect of anesthetic agents on cardiorespiratory-derived parameters from PPG)-, and/or PK plus PD-based system to control an infusor device to safely deliver IV agents. Drugs in this example include but are not limited to propofol, ketamine, fentanyl, and combinations of these agents thereof. The IV anesthetics could be mixed in a single syringe and delivered as a "cocktail" as the preferred embodiment, but alternately, individual IV anesthetics could be placed in different syringes and multiple infusion systems controlled by the system. Likewise, the system would preferably operate in a closed loop mode, but could also operate in an open loop mode. Taken together, a PK-, PD-, and PK+PD-based propofol infusion system that provides drug effects on respiratory and cardiovascular systems is therefore enabled and is easily implemented by those skilled in the art in light of the teachings provided herein.

Example 8

Military Environment—where Fluid Therapy is Tethered to Drug Therapy

While the following example provides considerations and embodiments of this invention which are particularly applicable in the battlefield context, those skilled in the art will appreciate, based on the rest of the disclosure and that which is described in this example, that there are many additional contexts, including civilian contexts, in which the embodiments described here are equally applicable. Thus, for example, for pilots at risk of GLOC, in firefighters at risk from fume inhalation, in sports divers, e.g. SCUBA divers, experiencing underwater seizures, heart attacks, loss of consciousness and the like, all could benefit by inclusion in their equipment of closed-loop or open-loop components of what is described in detail here under the rubric of the WARCARE™ system. Not all components need to be present in all such systems. At a minimum, what is required are the following components: at least one sensor adapted to measure at least one PD, PK, or PD/PK parameter of a subject; at least one processing system adapted to process signals acquired form the at least one sensor and adapted, on the basis of such processing, to instruct delivery of an agent to the subject; and at least one agent delivery system adapted to deliver to the subject an amount of agent instructed by the processing system. In preferred embodiments, as described below, the entire system is autonomous and self-contained. In other embodiments, the system is a closed-loop or an open loop system. In other embodiments, the system is in communication with external devices or people and is subject to optional external controls. In a highly preferred embodiment, the system includes a PPG, a nasal pressure sensor, an ECG sensor, and an integrated or separately emplaced nasal delivery system for delivering active agents, including in the form of fluids, gasses, aerosols, and/or non-aerosols, to the subject's nasal epithelium. The active agents could be stored in a container located near (or in) the nose, or at a more distant site from the nose.

Under battlefield conditions, there are often situations where warfighters are injured, but optimal trauma support is unavailable for extended periods of time. DARPA and DoD have been interested in systems that can administer care to wounded warfighters without outside intervention (Care Under Fire). We herein disclose the "Warfighter Autonomous or Remotely Controlled Advanced Resuscitation Ensemble" (WARCARE™ which allows warfighters the capability of providing pain control and if necessary, resuscitation due to blood loss to him/herself or to emplace a system on a colleague, especially in the far-forward combat zone. Additionally, as each warfighter is in communication with other warfighters locally and with remote medical support, the system as envisioned allows other warfighters, especially those trained in trauma care, and/or remote medical support to take over control of medication administration guided by data obtained from the SPOC system.

Modern warfighters have at their disposal a wide range of high technology equipment including communications, GPS, night vision goggles, improved body armour and helmets (to mitigate the effects of concussive injuries), etc. but at present battlefield medical support is extremely limited due to several overriding limitations. First, the individual warfighter may be inaccessible to colleagues during an on-going firefight. Thus, even when medically trained colleagues are available, they may not have immediate access to the injured warfighter. Second, the number of skilled medical personnel on the far-forward battlefield (Level 1 of 5 levels of medical care) is extremely limited. Thus, in the real-world of military medical care, stabilization is often delayed until transport from the battlefield is initiated.

While overall deaths (compared to earlier conflicts) have decreased dramatically during recent military operations as compared to military conflicts in the past (e.g. in the operations in Iraq and Afghanistan), due to intervention with improved medical technology, large numbers of survivors have extremely serious injuries that result in permanent disability. Often these injuries include traumatic brain injuries (TBI) and amputations of limbs. Finally, a large number (~18%) of injured warfighters suffer from Post Traumatic Stress Disorder, PTSD, which, along with the aforementioned injuries, costs the military and civilian healthcare systems unprecedented sums of money, not to mention the loss of quality of life to the individual warfighters. One recently identified approach to reducing the terrible toll of PTSD has been very early administration of opioids (e.g. morphine) to wounded warfighters. This, of course, cannot be done safely in the field absent the present invention.

WARCARE™, as disclosed herein, is a unique and novel system, method and apparatus that allows individual warfighters and/or other warfighters to begin administration of opioids, fluids and if necessary other medications to reduce blood loss, tolerate blood loss and/or decrease the extent of TBI and PTSD.

Figure 2:
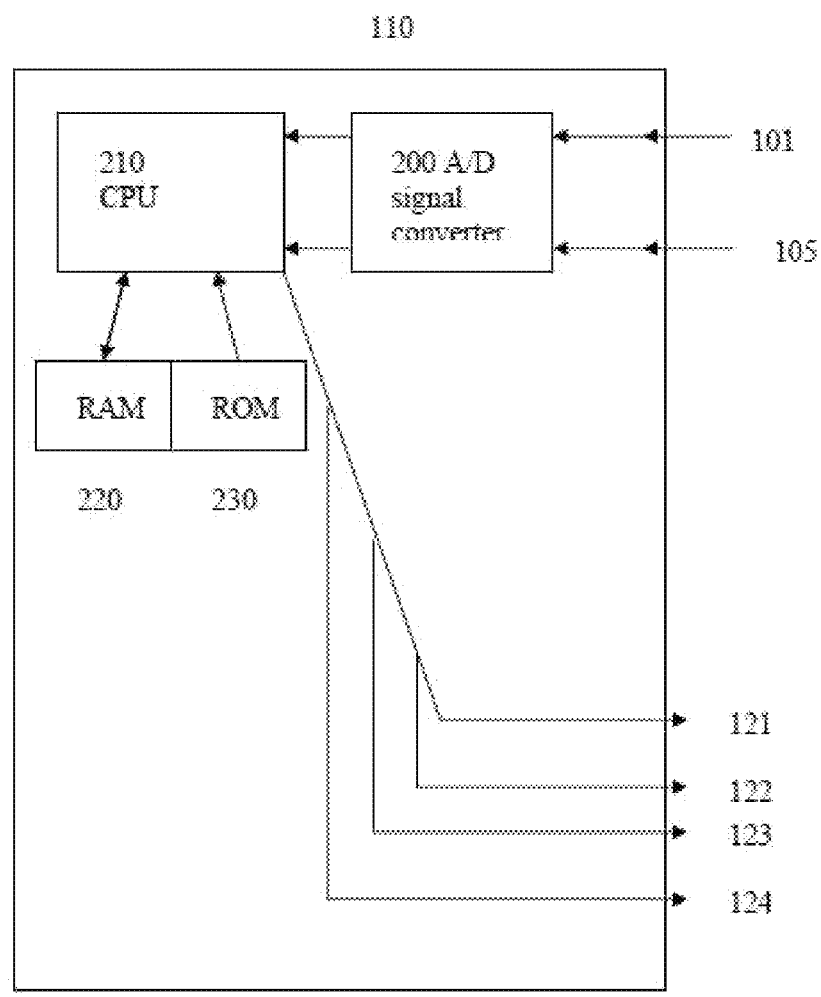
FIG. 2 provides an internal schematic representing PD, PK, or PD+PK and other relevant signals from the subject being converted into digital signals, if these are incoming as analog signals, and being processed via a central processing unit utilizing software implementing appropriate algorithms stored in Random Access Memory (RAM) or in Read Only Memory (ROM) or both, and then sending, via integrated or independent signal streams, controller information to the infusion pump.
Figure 3:
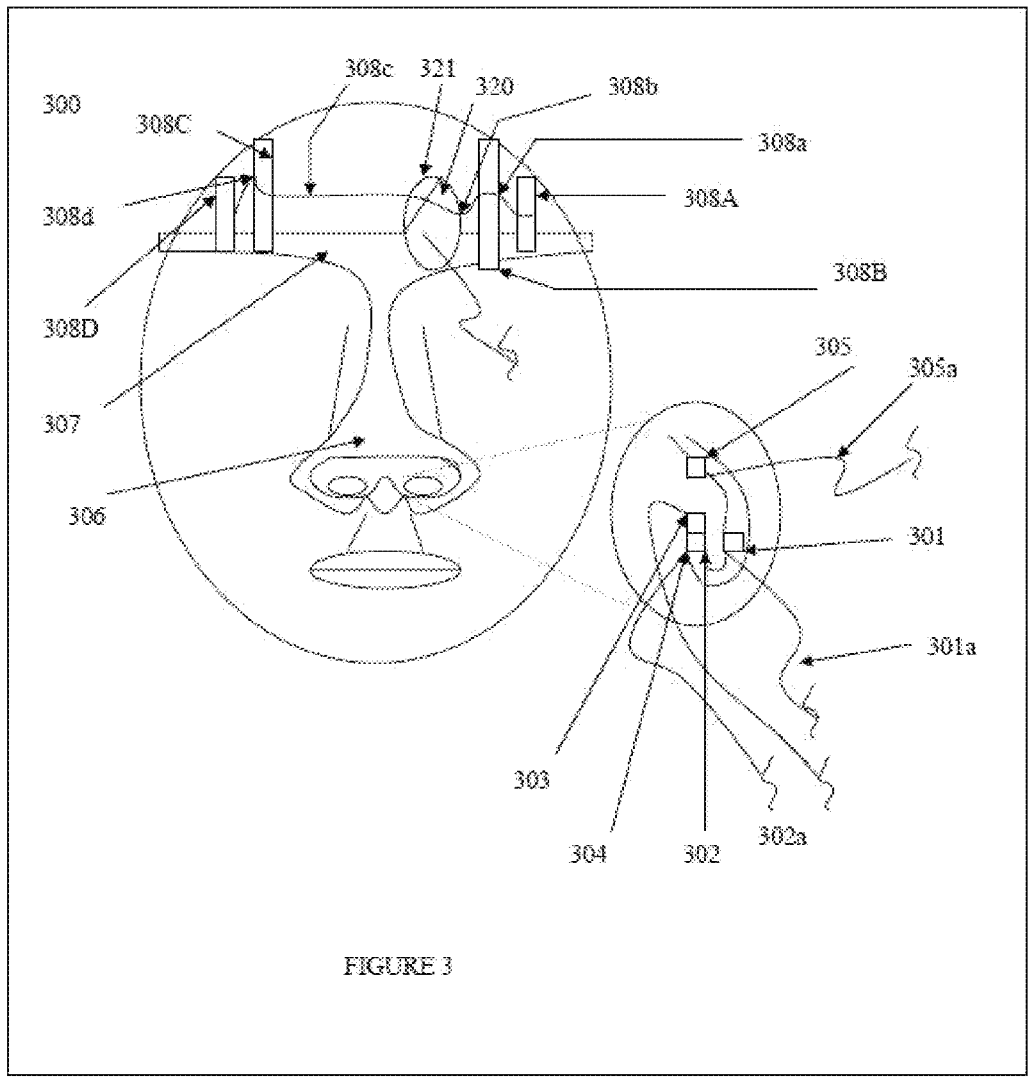
FIG. 3 provides a schematic representation of a preferred subject interface component of the system of the present invention whereby particular measurements of relevant PD, PK or PD+PK and other relevant signals are obtained from a Single Point of Contact (SPOC) on the subject (exemplified in the diagram by the nasal alae), and wherein, at the same time, fluids and drugs are delivered intranasally, e.g. to the mucosa of the nasal septum. This embodiment is particularly suited to the needs of combatants according to the WARCARE™ embodiment of the invention, but may be utilized also in civilian contexts.

WARCARE™ consists of some or all of the following elements (all components are preferably military specification compliant and hardened to meet the severe conditions encountered in combat situations). Numerals in the following description reference a figure (first numeral) followed by a second numeral for a given element, separated by a slash. Thus, 1/1 references element 1 in FIG. 1:

1. A battery pack or access to existing power in the warfighter ensemble 1/1.
2. An accelerometer or other motion (tilt, orientation, motion, elevation, or the like) sensing device 1/2 worn on the helmet of a subject 1/3 or other location on the head (e.g. behind the subject's ear) provides signals indicating whether a warfighter is actively moving or is inactive. This component is used primarily to "wake-up" the sensing system 1/4 so that it may remain in a standby status until needed. This reduces power consumption and the incidence of "false alarms". The accelerometer signal is a separate signal from PD and/or PK signals acquired by sensors for reading such parameters from the subject. Further, lack of movement by the warfighter especially in a recumbent (supine or prone) position may be indicative of a serious injury. The data from the accelerometer in conjunction with data from SPOC can be used assess whether a warfighter is injured or if the activity detected is very regular and vigorous, this may be indicative of seizure activity, as from a concussive head injury from an IED. Once wakened, the controller comprising a CPU 1/110 receives data 1/102, 1/102, 1/103, 1/104, 1/105 from the sensing device adhered to the subject 1/3, and, based on that acquired information, the controller/CPU 1/110, initiates delivery via a pump 1/120 of fluids and/or pharmacologically active agents 1/125, 1/126, 1/127, maintained in a secure compartment 1/130. These agents 1/125-1/127, for example, including but not limited to agents for providing analgesia, fluids and the like, are then infused via lines 1/122, 1/123, 1/124, optionally via a common line 1/121 (see discussion below where such a common line may be directed for delivery to the nasal septum). As shown in FIG. 2, the outputs via lines 1/101 and/or 1/105 are received by an analog to digital converter if necessary 2/200 which transmits the signals to the CPU 2/210, which has stored in RAM 2/220 and/or ROM 2/230 appropriate signal processing algorithms for interpretation of the incoming subject physiologic information 2/101, 2/105, for outputting instructions to initiate infusion to the subject of appropriate fluids and/or pharmacologically active agents, 2/121, 2/122, 2/123, 2/124.
3. As shown in FIG. 3, at least one, and preferably two SPOC sensor assemblies 3/300 each containing pulse oximeter components (LED 3/301 and photodiode 3/302), nasal pressure sensors, 3/304, and in one embodiment, one of two ECG electrodes, 3/305 (the other to be placed in the undergarments or on the torso of the warfighter). Such components are known in the art, for example, for obstructive sleep apnea (OSA) monitoring. As shown in FIG. 3, one SPOC sensor assembly, 3/300, is affixed to each nasal ala and joins below the bridge of the nose to form a single device that can be easily emplaced by the warfighter or another warfighter. In alternate embodiments, SPOC units consist of a unit that is attached to single alae. However, the redundancy, improved fixation and additional access to the nasal epithelium makes a dual SPOC a preferred embodiment according to this aspect of the invention.

4. Means are provided to fix the SPOC sensors securely to the subject. For example, the sensor assembly may be affixed by a retainer device, 3/306, which fits over the bridge of the warfighter's nose and/or up to the helmet or other fixation point on the forehead, for example, using a headband, 3/307. The forehead band, 3/307, communications ensemble or the helmet optionally contain reservoirs of medications and or fluids, 3/308, (3/308A, 3/308B, 3/308C, 3/308D, represent separate reservoirs with same or different fluids/medications), each of which is linked (via communication lines 3/308a, 3/308b, 3/308c, 3/308d to and activated for release of fluid/medications by the computer/CPU 3/320 which controls the closed-loop system, and other components/sensors of the system. The computer/CPU, 3/320, receives signals, 3/321, from the PD, PK or PD+PK sensors 3/301, 3/302, 3/305, affixed to the subject via communication line(s) 3/301a, 3/302a, 3/305a.

5. In one preferred embodiment shown in FIGS. 3 and 4, a small tube, 3/303, is incorporated into the assembly and is placed inside the subject's nostril and is pointed toward the nasal septum (nasal epithelium/mucosa, especially Kiesselbach's plexus and/or to the nasal epithelium/mucosa of the nasal turbinates, which delivers aerosols or non-aerosolized fluids, preferably in pre-metered doses of medications (e.g. opioids, anxiolytics, steroids, vasoactive drugs, and the like) using appropriate fluid delivery systems known in the art which are adapted for particular target delivery modes as described herein. Thus, for an intranasal delivery site, e.g. for delivery to the nasal epithelium, as shown in the drawings, a fluid nozzle aimed at the nasal mucosa, is incorporated into a nasal alar attachment housing. For intravenous delivery, a tube with an IV needle, such as those known in the art, may be used. Based on the present disclosure, those skilled in the art may develop any number of equivalent delivery means to those described herein for delivery to any appropriate subject. Thus, in alternate configurations, the delivery device may be a needle or catheter which is to be inserted intravenously, intraperitoneally, intraosseously, intracardiacly, or the like, but the non-invasive assembly for intranasal delivery is preferred.

6. Where utilized, the intranasal tube, 3/303, is connected to a drug delivery system capable of providing medication through the nasal epithelium delivery tube using aerosolized- and/or non-aerosolized-based systems 3/303. The aerosolized and/or non-aerosolized medication(s) is/are optionally stored in pressurized canisters, 3/308, adapted to provide metered doses upon actuation of a valve or a small pump that delivers aerosolized and/or non-aerosolized doses from a given container, 3/308, via delivery line(s) 3/309 connected to said nasal epithelium delivery tube 3/303. The components of this device should be tamper-proof to prevent use of stored medications for other than intended purposes. Alternatively, the canisters 3/308 may be housed elsewhere on the subject, such as on a belt, which may also house the computer/CPU 3/320, pump if required 3/321 and communication lines and fluid delivery lines (3/308a-d and 3/309, respectively). The medication canisters or backup or replenishment containers are optionally carried independent of the other components of the system by a limited number of individuals responsible for the canisters and made available to personnel in need of the given medications. Medications in the canisters are optimized to maintain pharmacological potency under a wide range of temperature and atmospheric conditions, for example, by inclusion in the medication compositions appropriate preservatives and the like. Using SPOC parameters to determine inspiration, medications can be metered to optimize delivery to the nasal mucosa.

7. Optionally, nitric oxide, histamine, methacholine or the like is included in the medication delivery system, either as part of the medication compositions or as a separate feed to the nasal mucosa, to increase permeability of the nasal mucosa to the delivered medications.

8. Highly concentrated doses of opioids (fentanyl, sufentanyl, and the like); opioid antagonists (naltrexone/naloxone for "recovery" if too large a dose of opioids is delivered); vasoactive drugs, particularly vasopressin; steroids (dexamethasone and others); dissociative agents such as ketamine; anxiolytics (benzodiazepines, gabapentin, pregabalin) and the like, are included as single component compositions which are separately deliverable to a subject in need of such agents, based on measurements of their PD parameters. Such medications are provided via separate infusion lines to the subject or may be combined for delivery through a single line.

9. Canisters or containers for medications and fluids, 3/308, are preferably adapted so that they can be removably but securely inserted into the system (e.g. canisters or container that can be snapped into the system by engaging clips and holding compartments adapted for protection and engagement of such canisters or containers) so that different medication combinations can be provided. At least 2 drug or drug combinations are separately deliverable in an embodiment utilizing two SPOC sensors (one on each nasal alar).

10. A small central processing unit (CPU), 2/210, 3/320, including algorithms/software stored in RAM, 2/220, and/or ROM, 2/230m facilitate closed-loop (servo) delivery of medications and control of the medical devices (sensors and infusion mechanics).

11. Small infusion pumps (e.g. ambIT PCA pump), 3/321, deliver volume expanders (hypertonic saline; dextrans) via subcutaneous, intraosseous, or IV routes when available. This also extends the range of the WARCARE™ to other levels (II-V) of medical care.

12. A second "peripheral" pulse oximeter sensor (fingers, toes, ear, etc) to provide information on volume status, or the status of an injured extremity. This is a standard finger/toe pulse oximeter probe/sensor which can be clipped (usually with a spring loaded design) to a finger or toe. The sensor usually contains to LED photodiodes (one emitting light in the IR range and one emitting red light). A photodetector evaluates the IR and red signals as well as the background signal sequentially and the pulse oximeter calculates the $SpO_2$ by calculations well known in the art. In the present application the sensor may be connected directly by a cable, or more advantageously by a Bluetooth or other wireless connection to the computer. The ability to simultaneously measure $SpO_2$ and PPG from 2 sites allows evaluation of volume status and/or status of a compromised extremity. See for instance U.S. Pat. No. 6,909,912 Non-invasive perfusion monitor and system, specially configured oximeter probes, methods of using same, and covers for probes.

13. Nasal pressure and/or flow sensors, 3/304, and/or PPG sensors, 3/301, 3/302, are utilized to detect phase of respiration and meter doses of medication only during the inspiratory phase.

14. Three levels of care provided in the battlefield prior to stabilization are provided by this system:
    a. Complete autonomous care by the warfighter.
    b. Other warfighters in the combat zone may assist, for example, by emplacing the SPOC sensor assembly if the warfighter is unconscious or unable to apply the assembly to him/herself. The system is still "autonomous" as it is not being remotely controlled.
    c. Remote communication of the vital sign information and control of the WARCARE™ system once the SPOC is emplaced. This is often referred to in the military as a "force multiplier" by allowing single medical personnel to monitor and treat multiple casualties.

Figure 4:
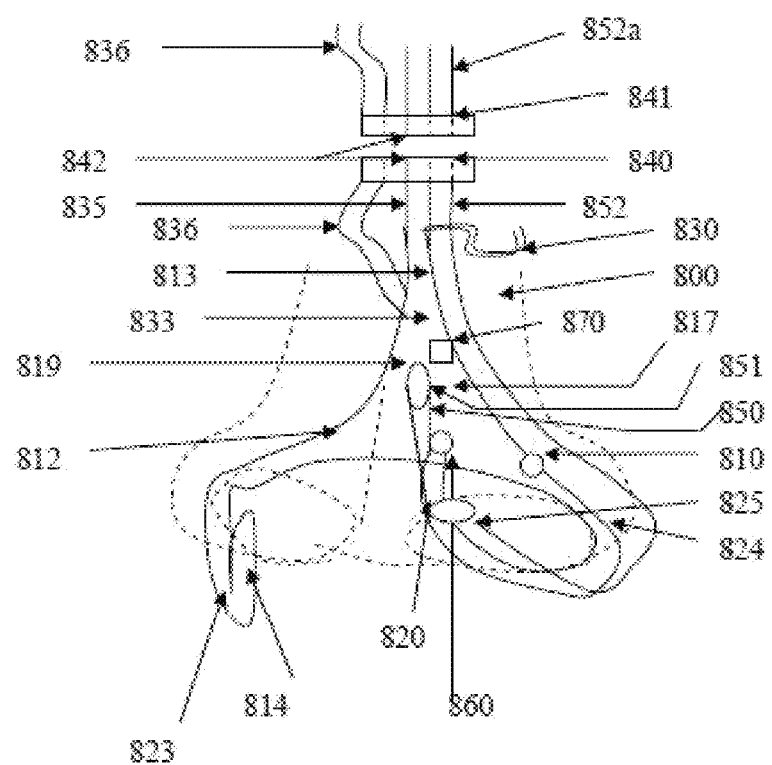
FIG. 4 provides a more detailed schematic representation of the subject interface at the nasal ala shown in FIG. 3 and a description of novel features of an SPOC probe embodiment according to this invention.

In FIG. 4, further details are provided for a preferred embodiment of the nasal SPOC system contemplated here, in which, integral with the acquisition of nasal pressure and PPG signals of the subject, the nasal sub-system is also adapted to delivery agents in fluid, gas, aerosol and/or non-aerosol form to the nasal epithelium. It should be noted, however, that the SPOC system may be adapted for emplacement, for example, on the ear of the subject, while the agent delivery subsystem is adapted for delivery to the nasal epithelium. That is to say, it is not necessary, and in some circumstances may be preferred, for the PD, PK or PD and PK signal acquisition site and the site of fluid or pharmacologic agent delivery to either be the same or different sites. Where fouling of the signal acquisition system by delivery of fluids, gases, aerosols and/or non-aerosols is a risk, it is preferred, of course, to separate the signal acquisition subsystems and the site of agent delivery of the agent delivery subsystems.

Turning to FIG. 4, a detail is provided for a novel nasal alar PD parameter measurement system which is integrated with a nasal epithelium agent delivery system. This subsystem is, for all intents and purposes, similar to the system 800 described in US2010/0192952, paragraphs 0056-0057, herein incorporated by reference, and, as modified below, specifically incorporated with respect to FIG. 4 herein.

A nasal probe embodiment 800 is configured for obtaining plethysmography readings and/or oxygen saturation readings from the user's nasal alar region. The nasal probe embodiment 800 comprises a base portion 813 which runs along the longitudinal ridge of the nose. At the distal end 833 of the base portion 813 is a bridge portion 819. The bridge portion 819 runs transversely across the nose and comprises a right flap portion 812 at one end and a left flap portion 817 at its left end. The right and left flap portions 812, 817, respectively, are positioned above the right and left nares of the user. The left flap 817 has attached thereto or integrated therewith at least one LED 810 or other light source. Extending down from the right and left flaps 812, 817 are a right extension 823 and a left extension 824. Attached to or integrated with the left extension 824 is a wing fold 820 that is configured to be inserted into the user's left nostril. The wing fold 820 has at its distal end a photodiode 825 attached thereto or integrated therewith. The wing fold 820 is designed to bend over and be inserted into the user's nostril such that the photodiode 825 is positioned directly across from the LED 810 located on the exterior of the user's nose. Extension 823 comprises wing fold 814 which is designed to be inserted into the user's right nostril. The positioning of wing fold 814 in the user's right nostril provides a counter force to the wing fold 820 which would tend to pull the probe 800 towards the left. Thus, the right flap 812, right extension 823, and right wing fold 814 act together to assist in securing the nasal probe 800 in place. The nasal probe 800 is provided with an adhesive material 835 and a peel-back layer 830. Before use, the peel-back layer 830 is removed and the adhesive 835 assists in securing the nasal probe 800 to the skin of the user's nose. At the proximal end 834 of the base 813, a connector 840 is provided. Wires 836 are provided in the nasal probe embodiment and run from the LED 810 and photodiode 825 up to connector 840. Furthermore, a flex circuit may be attached to or integrated with the probe embodiment 800 so as to provide the necessary wiring to the LED 810 and photodiode 825.

The connector 840 is adapted to securely mate with connector 841 via clips 842 to thereby provide electrical continuity for wires 836 to wires 836*b* which connect to the processing elements of the system described elsewhere.

In addition to the elements known from U.S. 20100192952 described above, the novel nasal alar subsystem of the present invention further includes additional key elements, novel to the invention disclosed herein.

A first novel key element shown in FIG. 4 is an agent (fluid, aerosol and/or non-aerosol or gas) delivery tube, 850, which runs along the nasal alar assembly into the nose and is oriented toward the intranasal epithelium at its distal end 851 (also shown in FIG. 3 as element 303). At its proximal end 852, the agent delivery tube 850 is integrated with connector 840 which, when coupled with connector 841, again via clips 842, to sealingly connect with extension 852*a* which runs to the agent reservoir(s) of the system described elsewhere, and which, on receiving instructions from the controller, also described elsewhere, results in administration to the subject of selected fluids and/or pharmacologically active agents. Of course, more than one separate tube line 840 may be provided, permitting more than one agent or more than one agent combination to be delivered to the subject at any given time. Ideally, the agent delivery tube internal diameter is sufficiently small to minimize any dead volume while at the same time being sufficiently large to permit ready delivery of agent to the subject. Those skilled in the art can achieve appropriate configurations based on this disclosure without undue experimentation.

A second novel key element shown in FIG. 4 is a nasal pressure sensor, 860 (also shown in FIG. 3 as element 304). The nasal pressure sensor detects small changes in pressure near the nasal opening caused by breathing. Typically these changes are less than 2-3 cm H20 (0.03 PSI) must be very sensitive and accurate. Even during mouth breathing, pressure fluctuations can be detected near the nasal opening, although the pressure changes are even less than described above. Typically, a nasal pressure measurement system consists of a small bore sensing line inserted into the nasal opening that connects to a very low pressure sensor located a small distance from the sampling point to minimize pressure losses in the sampling line (although in theory, a pressure sensor could be embedded in the nasal opening, this is not currently implemented due to the size of the precision pressure sensors). Pressure fluctuations measured by the pressure sensor (various types of pressure sensors are common and known to those skilled in the art) are typically temperature compensated and digitized for processing by a digital processing system. In addition to the decrease in pressure during inhalation and increase in pressure during exhalation, the shape of these waveforms can indicate important aspects of the breathing such as effort to breath, occlusions or high resistance during inhalation or exhalation, among other attributes).

In addition to a pressure sensor, flow sensors can also be used. Pressure sensors are typically considered to have more information related to wave shape, but flow sensors can be very simple thermistors or other devices that can be directly inserted into the nasal opening to reduce the need for tubing.

A third novel key element of the shown in FIG. 4, is an ECG probe, 860 (also shown in FIG. 3 as element 305, along with its communication line 305a) which provides the system of this invention the ability to secure direct cardiac signals. Along with a second lead which can be attached to the undergarments of the subject or directly to the skin as a conventional ECG electrode is attached, a single lead ECG can be obtained. Addition of an ECG signal allows not only the detection of the heart rate, but detection of arrhythmias. Also several derived signals such as pulse transit time are determined by using the ECG signal in conjunction with the PPG signal.

Through use of the novel alar probe design described above, (in addition to the previously appreciated superior probe position on the lateral side of the nostril just behind the prominent part, which is referred to as the fibro-areolar tissue, see U.S.20100192952), the probe of the present invention, for the first time, also facilitates closed-loop as well as open-loop delivery of fluids and pharmacologically active agents, non-invasively, to a site of excellent access and bioavailability (the nasal epithelium). It also provide more accurate measurements of the subject's breathing patterns (via the nasal pressure transducer sensor), and ECG readings. Of course, in various embodiments, not all of these elements are required to be present. For example, the agent delivery tube and the nasal pressure sensor may be present, while the ECG sensor may be absent or located elsewhere. Likewise, as mentioned above, the agent delivery system may deliver agents to the nasal epithelium, while the SPOC may be emplaced at the subject's cheek or ear. Alternatively, the SPOC may be emplaced at the subject's nose, while the agent delivery system delivers agent to the subject at any other convenient site, including but not limited to intraperitoneally, intravenously, sublingually, etc. Those skilled in the art will appreciate that the present system accommodates a large number of permutations and combinations, without departing from the central teachings of this invention. It will also be appreciated that a similar arrangement of components may be included for both nares of a subject as described above, such that there is redundancy in the system and, in addition, there are additional options available for providing different drug combinations to the left and right nasal epithelia.

Thus, in a preferred embodiment, the alar probe 800 is dimensioned so that placement onto the fibro-areolar region is optimized for the user. Other embodiments are contemplated as well, including clips, hooks; and reflectance designs for either inside or outside nose. which could be inconspicuous and would be especially advantageous for ambulatory and long term use.

The WARCARE™ system optionally remains in place as the warfighter is transferred to higher levels of medical care for both monitoring and drug therapy. Once IV access is obtained, drug delivery can be switched to this route. Preferably, the WARCARE™ system remains in place through all levels of medical care and it preferably is adapted to interface with other medical treatment and monitoring systems.

In one embodiment, where the warfigther is undergoing surgery or anesthesia/conscious sedation is otherwise required, a propofol sensor/monitor can be attached to the SPOC array, or alternatively in-line with an endotracheal tube, laryngeal mask airway, etc. to allow physicians and physician extenders to provide anesthesia/conscious sedation with propofol and propofol "cocktails" (e.g. combinations including analgesics and Ketamine).

The complete WARCARE™ ensemble preferably adds only a small fraction to the weight (normally 60-80 pounds) carried by the warfighter.

In real-world practice, an injured warfighter who is conscious is able to rapidly emplace the WARCARE™ system on his/her nose or other appropriate site on the subject and the system immediately activates and begins providing pain medication and other medications based on the sensor data interpretation and algorithms. If the injured warfighter is incapacitated, a fellow warfighter emplaces the WARCARE™ SPOC system on the injured warfighter. Additionally, since each warfighter preferably carries medications adapted for insertion into the WARCARE™ system, they could be used on a wounded warfighter, thus increasing the amount of medication available in the field. Alternatively, or in addition, the WARCARE™ assembly is in place as in integral part of the combatant's helmet and/or telemetry gear.

A key feature of the WARCARE™ system is its ability to deliver medications in a timely manner through a site where absorption is almost as reliable as IV injections.

Multiple studies have shown that the nasal epithelium absorbs about 60-80% of the dose of an IV injection of the same quantity of medication, (see, for example, Velhorse-Janssen, et al., 2009, "A Review of the Clinical Pharmacokinetics of Opioids, Benzodiazepines, and Antimigraine Drugs Delivered Intranasally", Clinical Therapeutics, Vol. 31, Number 12, pp. 2954-2987; Moksens et al., 2010, J. Opiod Manag., 6(1):17-26, "Pharmacokinetics of intranasal fentanyl spray in patients with cancer and breakthrough pain"; Dale et al., "Nasal administration of opioids for pain management in adults", Acta. Anaesthesiol Scand. 2002; 46:759-770). This will likely be true even if a warfighter is hypotensive since this area of the nasal septum is richly supplied by arteries which are branches of both the internal and external carotid. Likewise, vasopressin (unlike alpha adrenergic vasopressors) is unlikely to cause intense local vasoconstriction in the nasal area, thus allowing absorption of other medications given at the same site.

It is important to note that the WARCARE™ system is adapted to provide both the initial monitoring and medication delivery to the injured warfighter and then continue to provide monitoring as well as medication delivery by conventional routes once IV access is obtained. WARCARE™ is a force multiplier as it allows a limited number of skilled medical personnel to monitor and treat a large number of injured warfighters throughout their transport from Level I to Level V care.

The accelerometer or like motion and/or orientation detection sensor, monitors whether a warfighter is actively moving or has suddenly ceased to move.

Preferably, the accelerometer or like motion sensor is used to limit the power consumption of the WARCARE™ system by maintaining it in "sleep" mode until it senses a sudden change in the war fighter's level of activity. In one embodiment, the accelerometer is adapted to detect very regular but intense body movement indicative of seizure activity, in which case a signal from the accelerometer sensor is processed by the controller to provide a benzodiazepine or other antiseizure medications if the WARCARE™ system is in place or once the SPOC assembly is emplaced by a fellow combatant. The accelerometer would also be capable of monitoring the body position of the warfighter. A long period of inactivity in the prone or supine position is optionally programmed into the system to trigger a remote alarm so that other warfighters are alerted to determine the status of the warfighter being monitored. Likewise, the accelerometer or other motion sensor is used as an additional monitoring parameter while a warfighter is being treated by the WARCARE™ system. A sudden reduction in movement is optionally programmed into the controller as an indication of inadequate pain control in the setting of acceptable vital sign parameters, while a reduction in movement coupled with unacceptable vital signs is optionally programmed into the controller to be interpreted as an urgency requiring provision of resuscitative measures. In some instances, the accelerometer or alternate motion sensing component of the WARCARE™ system is the first indication of a problem with a warfighter, in some instances, even prior to the emplacement of SPOC on the subject—provided the subject is carrying the system somewhere in his/her kit.

Example 9

Photoplethysmography Sensor and Nasal Pressure Sensor Signal Processing and Control of Infusion Pump In an exemplary embodiment of this invention, a prototype has been developed to confirm the working principles outlined herein above. In this prototype, photoplethysmography sensor signals and nasal pressure signals are acquired from a subject, the signals are processed and output controls to an infusion pump are produced to control drug delivery. This example demonstrates that the civilian and military applications of the present technology are operative with these and a wide variety of other possible sensors.

A subject was fitted with a nasal photoplethysmography unit and a nasal pressure transducer unit. Raw data from the photoplethysmography (PPG) sensor and the nasal pressure sensor were acquired and processed as described below to return heart rate, breath rate, and obstruction level information with respect to the subject. These parameters are then used to govern pump titration rate.

As discussed generally above, signal acquisition from the subject may be initiated manually, or signal acquisition may be initiated automatically, for example, as a result of accelerometer signals to the control unit indicating a change in subject status, including, but not limited to, a beyond threshold period of inactivity, excessive, repetitive shaking, indicative of seizure, rapid change in vertical to horizontal orientation, indicative of a fall, or other pre-determined motion-related parameters. Of course, other motion sensing-means besides an accelerometer may be utilized for this purpose.

Definitions, Acronyms, and Abbreviations

DC=The low frequency component of either the red or infrared channels of the PPG sensor found by subtracting the AC component from the raw signal.
AC=The cardiac or high frequency component of either the red or infrared channels of the PPG sensor
DC=The low frequency component of either the red or infrared channels of the PPG sensor found by subtracting the AC component from the raw signal.

Algorithm Description
  The algorithm can be broken up into three main phases:
  1. Filtering and preprocessing: streaming data is separated into the channels that will be used in parameter calculation and individual breaths and heart beats are identified and marked.
  2. Parameter Calculation: the main predictive elements of the model are computed
  3. Model output generation: the parameters are combined into the desired outputs
Filtering and Preprocessing
  Here the IR and RED channels of the PPG signal are first sorted into AC and DC channels using a novel algorithm. Whereas a standard low pass filter is typically used to separate the DC component from the raw PPG signal, this device uses the following unique approach:
  1. An initial guess of heart rate (such as 60 beats per minute) is used at the onset of processing.
  2. This heart rate is converted into an appropriate search window (such as 1.5/(heart rate)).
  3. A local maximum is found in the raw PPG signal within this search window. This is the peak of a single heart beat.
  4. A new estimate of heart rate is found by subtracting the time of previous maximum from the current maximum. This new estimate of heart rate is typically averaged with previous heart rate estimates for stability.
  5. The "valleys" are found by finding the minimum value of the raw PPG signal between the current maximum and the previous maximum.
  6. If there is more data, return to step #2 and repeat.
  Using this approach, the locations of the peaks and valleys for each heart beat are identified and stored in a table.
  Halfway between each peak and valley a "midpoint" is identified. The DC component is then found by a linear interpolation between these midpoints.
  This approach is different from traditional approaches to finding the DC component in that it produces an estimate that does not have a lag or time shift relative to the raw PPG signal. Rapid changes in DC baseline are, therefore, more accurately captured using this approach.
  The AC component is then found using a point-by-point subtraction of the DC component from the raw PPG signal.
  Next, the DC component is filtered using a band-pass butterworth filter to find the respiratory component of the PPG signal. Two possible ways the band-pass cutoff frequencies can be determined are:
  1. Use a set range based on common breath rates (such as 1 to 0.1 Hz)
  2. Use the nasal pressure signal to determine the average breath rate and then center the filter cutoffs over that breath rate.
  The nasal pressure signal is then also filtered using a band-pass Butterworth filter to remove artifacts and noise. Filtering the nasal pressure signal helps identify prominent breath features (peak inhalation, peak exhalation, etc) and helps reject noise and motion artifacts.
  Finally the individual breaths are identified in the pressure signal. The start-of-inspiration (SOI) and end-of-breath (BOB) as well as the peak inhalation and exhalation are found and stored in a table.
Parameter Calculation
  From the nasal pressure and two PPG channels (IR and RED) a wide range of parameters can be calculated to help predict respiratory and cardiac phenomena. Some of these parameters include:

Nasal Pressure Amplitude: the distance between the peak of inhalation and the peak of exhalation for each breath averaged within a time window (1 minute for instance)

Nasal Pressure Breath Rate: The average breath rate found within a window of time.

Nasal Pressure Amplitude Variance: the variance of all the nasal pressure amplitudes found within a time window.

Nasal Pressure Breath Period Variance: the variance of the individual breath times (end-of-breath time minus start-of-breath time) for each breath within a time window.

DC Drop: the distance between the base of a DC drop and its baseline (baseline is typically the average DC value over a larger time window)

DC Drop Duration: the time it takes for the DC component to return to baseline after a drop from baseline.

DC Drop Area: the area found by integrating the signal (DC Baseline—DC Component) during a DC drop from baseline.

AC Heart Rate: the average heart rate found in the AC component within a time window.

AC Heart Period Variance: the variance of the individual heart beat lengths within a time window.

AC Amplitude: an average of the individual heart beat amplitudes (maximum minus minimum) within a time window.

AC Amplitude Variance: the variance of the individual heart beat amplitudes within a time window.

SAO2 Drop: the drop in the blood O2 saturation found by converting the IR and RED PPG signals into an estimate of blood oxygenation (ie the more traditional use of the PPG signals)

PPG Resp Energy: the energy in the respiratory component of the PPG signal within a time window.

Model Output Generation

The parameters described above are typically converted into unit-less "percent" values. This is done by calculating a baseline using a large time window and then each parameter is converted to a percent-change-from-baseline. After this conversion, the parameters are then combined in appropriate proportions to generate model outputs. Most commonly, these parameters are combined using a simple linear combination though a more advanced method such as tap-delay lines or neural networks can also be used.

Figure 7:
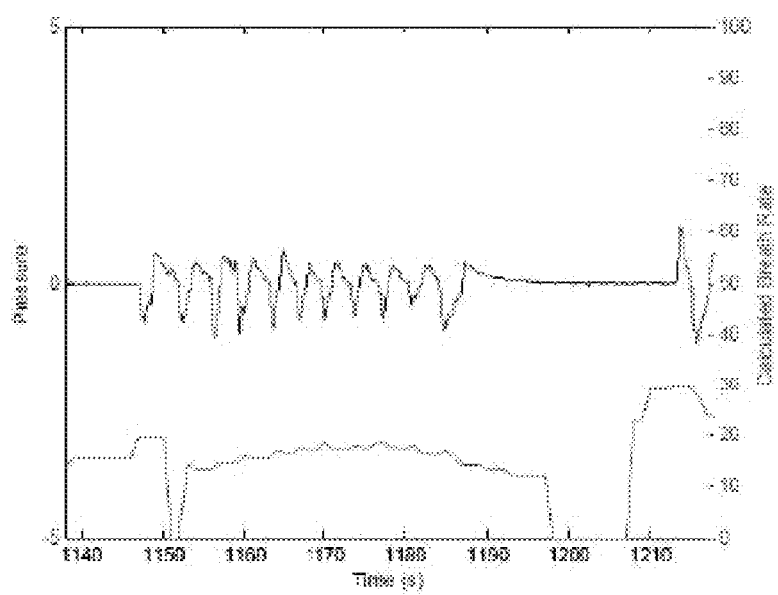
FIG. 7 shows the system's ability to detect another respiratory pause.
Figure 8:
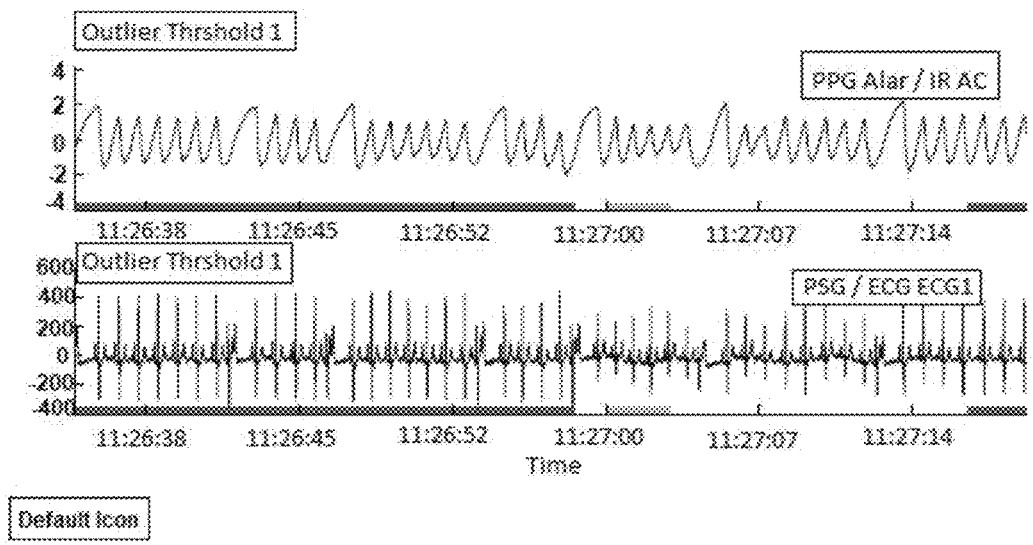
FIG. 8 shows synchronization of PPG and PSG data using a genetic alignment algorithm to optimally match the PPG AC signal with the PSG ECG signal

The parameters described above can be combined to produce signals that regulate the titration of the infusion pump. The two main model outputs that control the pump are "Breath Rate" and "Obstruction Level". Other indications of respiratory or cardiac distress can also be inferred from these parameters and pump infusion rate can be adjusted accordingly Algorithm Validation Results A preliminary validation process has been conducted by collecting data on subjects simulating respiratory failure and visually inspecting the prototype's output. Some examples of these tests are shown in FIGS. 7 and 8.

Based on the processing of the PPG and nasal pressure signals, the system of this invention is able to select which drugs, and the quantities of such drugs to be administered to the subject. Of course, ongoing iterative application of given pharmacologic and fluidic interventions are reflected in the ongoing monitoring of PD, PK or PD and PK parameters acquired from the subject, allowing for dynamic modifications to the intervention, within appropriate pre-set limits defined by qualified medical personnel for a given context.

Example 10

User Interface

In preferred embodiments according to this invention, the closed-loop or open loop system or apparatus is emplaced on a subject, either by the subject or a colleague, physician, or the like. On being emplaced, the system initiates, conducts an internal self check to ensure that it is operating properly, that it has sufficient power for reliable operation, that it is properly interfaced with the subject and is able to acquire appropriate PD, PK, or PD and PK signals from the subject. The thus emplaced and properly operational system, in a preferred embodiment, then goes into a sleep or standby mode in which operational parameters are minimized along with minimal power consumption.

On being stimulated by an appropriate wake-up signal, which may be the subject pressing a start button, or an integrated motion sensor such as an accelerometer recognizing a motion state that is defined as requiring wake-up (e.g. excessive vibration, or no motion at all by the subject, or a sudden change in vertical to horizontal orientation), or due to an external telemetry signal from a central monitoring station, the system wakes up, quickly performs an operational self check and then measures appropriate PD and/or PK or other parameters for the subject. If all parameters check out as being normal or within pre-defined acceptable tolerances, the unit may once again enter a sleep mode. If any parameters are out of pre-defined tolerance, the unit immediately initiates delivery to the subject appropriate agents (fluids and/or nutrients or pharmacologically active agents), to bring the subject's parameters back within pre-defined acceptable tolerances. In the WARCARE™ embodiment described above, in a preferred embodiment thereof, the unit is entirely self-contained and autonomous and requires little or no intervention from the subject themselves or from external personnel.

Figure 5:
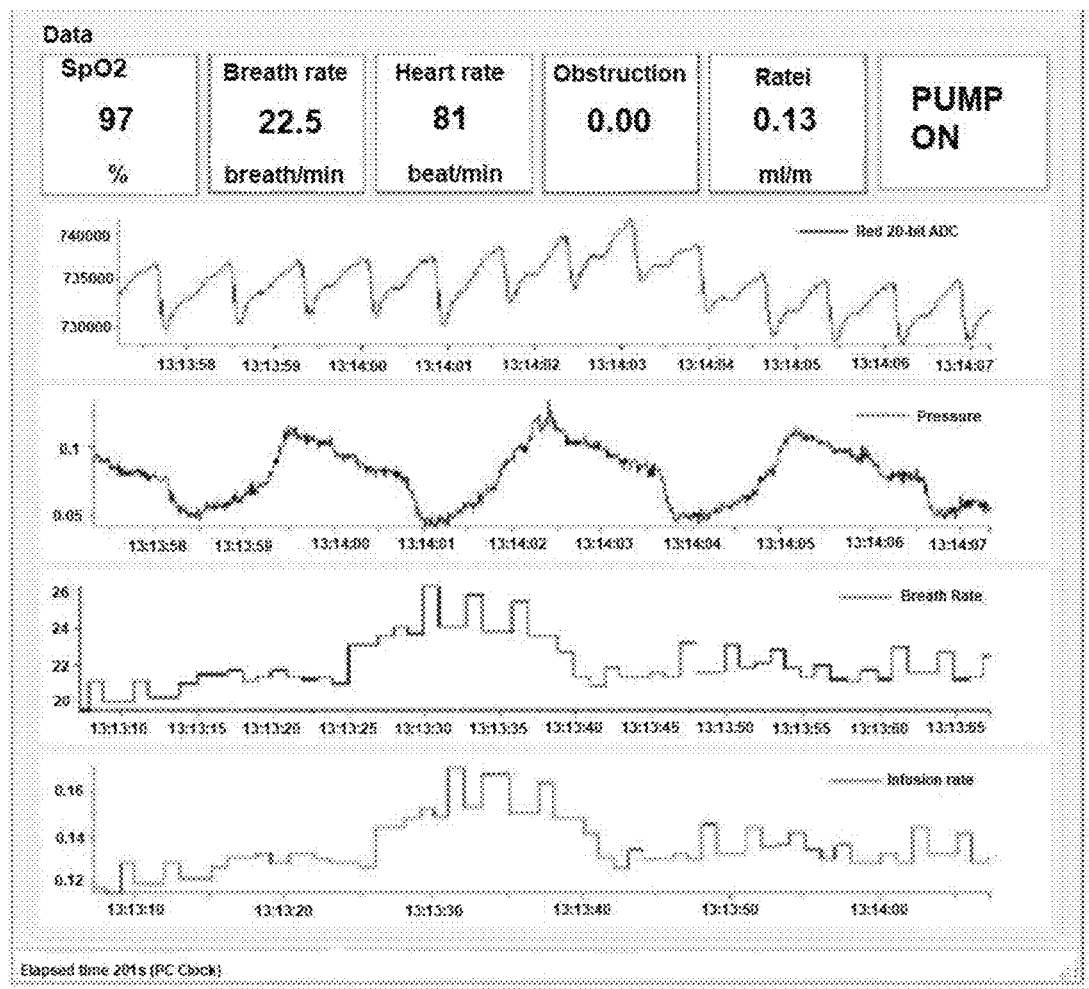
FIG. 5 provides photographic depiction of the user interface of a prototype of one embodiment of the apparatus according to this invention. the "Red" signal shows the heart beats in the pleth; in blue, pressure waveforms reveals the decreases in nasal pressure during inhalation and the increases during exhalation, occurring more slowly than the heart beats; the breath rate and infusion rate are on a slower time scale in the bottom two plots; an additional box is included that shows the "Obstruction level".
Figure 6:
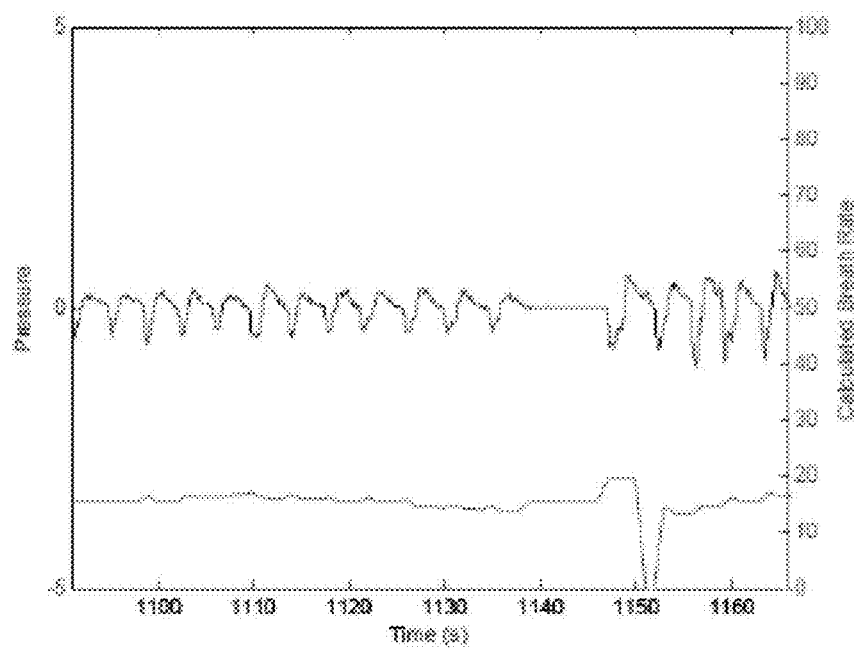
FIG. 6 shows the raw pressure signal and model output for breath rate during a small pause in breathing.

In an operational prototype of the present invention, a graphical user interface is provided, shown in FIG. 5. This is not intended to limit the interface options that are available in the apparatus or system of the invention. Rather, this is intended only to show that at the date of filing of this application, the system according to this invention is operational and in the possession of the inventors and to further extend the written description, comprehensibility and enablement for the present invention.

Turning to FIG. 5, it the following elements can be seen and are understood as follows:

At the top of the figure, a variety of settings for the pump control software are shown, including the minimum and maximum thresholds that determine when the pump is fully on and when it is fully off. There is an override for the pump and breath rate to permit manually setting the pump or the breath rate.

Numeric values are shown for breath rate, heart rate, and ratei, (ratei is the current infusion pump setting (rate of infusion), which changes with breath rate), and an indicator that the pump is currently on.

The red signal is the red signal from the pulse-oximeter. There are two raw signals from the pulse-ox, infrared and red that are used in combination to determine the oxygen saturation. The red signal is less sensitive to saturation changes and thus provides a more stable signal for PPG processing for purposes of this invention.

The AIN 0 signal is the nasal pressure indicating the change in pressure in the nasal opening during breathing. AIN is analog input 0 from the A/D converter, which is obtained from the pressure sensor. This signal very accurately represents breathing, including when mouth breathing is occurring.

The first two graphs are 10 second plots showing the real-time breathing and pulse. The next two graphs are 1 minute long graphs of breath rate and infusion rate, showing how the infusion rate changes over time based on the measured breath rate.

The Red 20 bit ADC value is obtained via the oxypleth pulse oximeter. In practice, this would be the value coming directly off the photodetector when the red LED is pulsing, (typically, pulse oximeters pulse red and infrared light alternatively into a single photodetector). Both signals are obtained by the PC via the serial port of the oxypleth.

The AIN0 is the nasal pressure signal obtained through a nasal oxygen canula and is converted via a very sensitive pressure transducer (Microswitch, part #DCXL01DS) and then A/D converted via an A/D converter.

The breath rate is calculated from the nasal pressure signal by detecting changes in pressure during the breathing signal, or alternatively can be calculated via changes in the PPG signal.

The infusion rate signal is sent to the infusion pump to dynamically control it. Currently, this signal is derived from the breath signal (which comes from the nasal pressure signal, but could also come from the pleth/red signal). When the breath rate is high, the pump is on fully. When the breath rate falls below the upper threshold, the pump rate decreases until the lower threshold, at which point it turns off. This represents one simple method of controlling the pump. There are much more sophisticated ways in which those skilled in the art could modify this, based on the present disclosure, including, but not limited to, by using breathing pattern characteristics, such as entropy of the breathing pattern, and the like.

The DLL=true shows a debug statement indicating that the DSP algorithms are being called and returning valid data (e.g. the interface software collects the data and sends it to the DSP algorithms in a separate DLL. When the DLL successfully processes the waveform data and returns the information to the user interface, it returns the data, this indicator says true.

Example 11

Signal Acquisition, Processing and Statistics

This portion of the disclosure summarizes the results achieved in the development of the Single Point of Contact Diagnostic System (SPCDS, or SPOC). The goal of the project was to develop and validate algorithms to calculate RDI (Respiratory Disturbance Index) for a single point of contact diagnostic system consisting of a nasal pressure sensor and a nasal pulse-oximetry/plethysmography sensor. The following bullets summarize the work described hereinbelow:

Polysomnography (PSG) and photoplethysmography (PPG) data was obtained from 35 subjects and scored manually by a trained research technician. The data on the first 20 subjects will be used as a training set, and the data on the remaining 15 subjects were used as a validation set;

Optionally, a study to collect data on up to 10 subjects with epiglottic catheter as a measure of respiratory effort was included;

Preliminary assessment of the prototype AHI estimator based on new patient data and analysis/integration of appropriate algorithms and analysis is provided summarizing in-sample data;

Statistical Analysis: To determine the accuracy of the SPCDS, RDIs were calculated for each study and compared to manual scoring. Receiver-operator characteristic curves can be constructed for the RDIs calculated to assess the performance of the automated algorithm across the spectrum of SDB severity (RDI cutoffs of 5, 10, 15, 20 and 30 events per hour for defining obstructive sleep apnea). The area under the receiver-operator characteristic curve were calculated for each threshold and reported with the standard error and the limits of the 95% confidence interval. Positive likelihood ratio, negative likelihood ratio, optimum sensitivity and specificity were calculated for each threshold. An epoch by epoch assessment of agreement for the detection of respiratory events was conducted.

The outcome of this work was the development of a prototype algorithm validated on 20 subjects recruited from a sleep lab.

The operation of the prototype was validated using analysis of a 15 patient test set utilizing the statistical methods described above and below.

Synchronization

Precise synchronization is an important prerequisite for accurately analyzing the SPOC data. There are three types of synchronization that we implemented during this project. First, low level synchronization involves the alignment of the pulse-oximetry/photoplethysmography (PPG) data with the polysomnography (PSG) data. Second, to optimally detect events, a portion of the parameters that are delayed indicators of events (e.g. post-event parameters) must be "aligned" with the parameters that are already synchronized with the events. And third, "predicted event to scored event" synchronization to allow for the matching of SPOC-labeled events with manually scored events is necessary to determine sensitivity and specificity values.

The accurate synchronization of the PSG and PPG data was a major task. The PSG data is collected via the Alice system and the PPG data is collected using a NICO monitor connected to a PC utilizing a LabView program. The LabView program sends the PPG data along with sync pulses to the Alice system to ensure that the data remains aligned. Unfortunately, the data typically slowly drifted out of alignment, even when using the sync pulses. The sync pulses only ended up providing a rough but inaccurate alignment of the data. We utilized a genetic alignment algorithm to match the two data streams by maximizing the correlation between the ECG channel in the PSG and the AC signal in the PPG. The results for each patient were validated manually and the alignment was determined to be excellent. An example alignment is shown in FIG. 8.

The second synchronization effort is one of aligning parameters that correspond to events with parameters that correspond to post-event phenomena. For instance, the nasal pressure signal drops during an apnea event, but the pleth DC signal drops during the post-event time. In order to maximize the classification capability of these signals, it is desirable to shift the pleth DC signal back in time to be better aligned with the nasal pressure signal. To optimize this process, we determined the maximum area under the curve (AUC) of each parameter's event-prediction ROC curve. We then shifted the parameters and determined the shift that produced the largest AUC (e.g. the best prediction). This synchronization dramatically increased the discrimination provided by these "post-event" parameters.

The third synchronization, aligning the predicted and actual events for sensitivity analysis, will be described in greater detail in the Results section.

Model Optimization

To derive a predictive model, there are multiple levels of optimization that can be utilized. First, individual parameters must be conceived, implemented, evaluated, and optimized. Second, individual parameters must be combined optimally to create the desired model.

The first step in creating a model to detect events is to create appropriate parameters that capture information of interest. We started the project with a literature review and several brain-storming sessions to determine physiologic effects we were hoping to capture mathematically from the data. Once the physiologic effects are identified, parameters are coded and evaluated to determine how well they capture the information intended and how well the information predicts the events. Each physiologic effect (e.g. venous capacitance change, reflected by a change in pleth DC value) may have several possible parameters that attempt to capture its useful information (e.g. area in the DC drop, DC drop depth, DC drop time, etc.) and each parameter may have several sub-parameters that need to be optimized (e.g. window width to determine DC baseline for calculating DC drop). All of these parameters and sub-parameters were optimized using the AUC of an ROC curve generated by separating event breaths from non-event breaths. This AUC methodology allowed us to optimize the individual parameters without having to do end-to-end comparisons of event detection (e.g. event synchronization, RDI calculation, etc.). The AUC methodology provides a method of maximizing each parameter's ability to separate the event vs. non-event distributions.

The physiologic effects we attempted to parameterize were:
  Venous Compartmentalization
    Rise of DC during events
    Fall of DC during arousals
    Slope of DC "recovery"
    Envelope changes in the BR signal.
  Saturation:
    Drop/Rise in $SpO_2$ over IR during event/recovery.
    Desaturation slope
  Respiratory System:
    Amplitude of flow and pressure drops/rises during events/arousals.
    Breath Amplitude variability
    Shark fin pattern during early part of occlusion
    Breathing effort pattern from IRDC curve.
  Cardiac System:
    HR & HR variability
    AC amplitude and AC amplitude variance
  Nervous system:
    HR variability, Breath Rate variability, IR DC variability Because many of the parameters are based on characteristics of breathing, we decided to first parse the data files into breaths to allow for a consistent methodology for parameterization and averaging. Breaths were determined based on the nasal pressure signal. During apneas when the breathing was not easily determined, an average breath rate was utilized to parse the data. The training set was then labeled from the manual scoring table, producing breath-by-breath labeling of the events. Each parameter was then calculated for each breath and the breath-based labeling and parameters were used to calculate ROC curves. Breath-by-breath analysis is not optimal since an event might be 3-5 breaths and a parameter might miss the first and last breath, for instance. This technique, however, does provide a low-complexity methodology for determining the separation provided by the parameters and allows for optimization of the parameters and sub-parameters.

The parameters derived from this analysis consist of:
  5 Nasal pressure parameters
  6 $SpO_2$ parameters
  9 Pleth cardiac parameters
  8 Pleth low frequency parameters
  3 Pleth breath parameters (bandpass filtered at breath rate)

Figure 9:
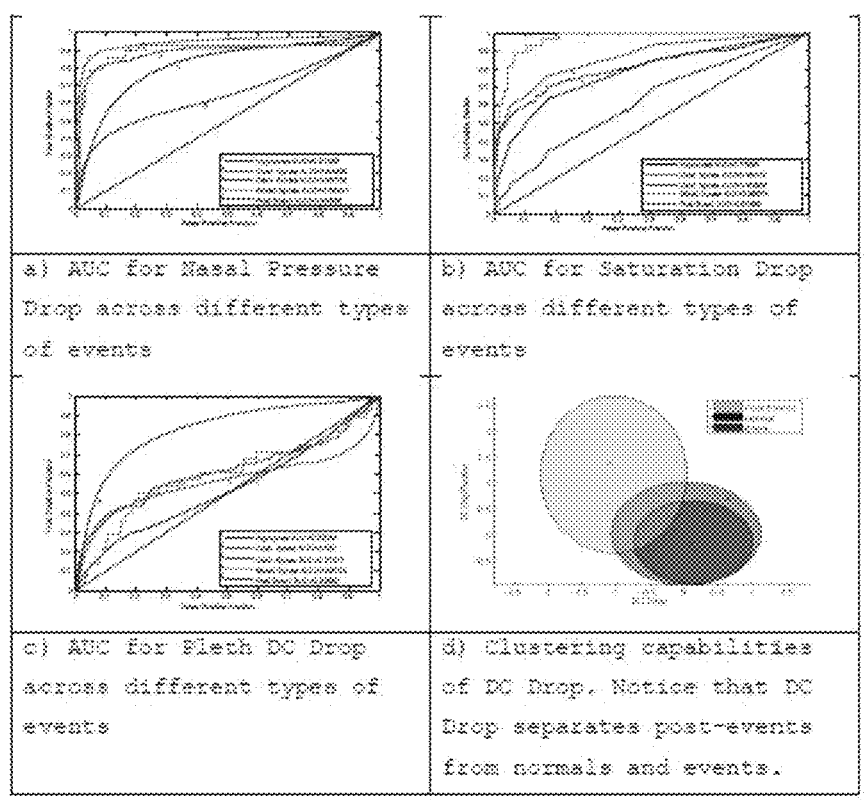
FIG. 9 shows optimization of individual parameters (a) AUC for Nasal Pressure Drop across different types of events; (b) AUC for Saturation Drop across different types of events; (c) AUC for Pleth DC Drop across different types of events; (d) Clustering capabilities of DC Drop. Notice that DC Drop separates post-events from normals and events.

FIG. 9 shows several plots indicating the performance of the individual parameters on breath-by-breath classification.

Once the individual parameters are optimized, the next step is to create multi-parameter models that maximally capture the information and coupling of the individual parameters as well as the temporal structure of the data. An important consideration in multi-parameter modeling is that it is the unique (independent of other parameters already in the model) information that a parameter adds to the model that makes it valuable, not its individual ability to separate the classes. Another important point is that optimization of any model requires good criteria. We determined that the best result is one that maximizes multiple criteria simultaneously: correlation with RDI, Kappa statistic for epoch-by-epoch confusion matrices, and diagnostic agreement. Although this complicates the optimization process, the performance surfaces of the models was not steep or highly non-linear, so optimization of multiple criteria was possible without excessive effort.

To use these statistics for optimization, however, we needed to implement several algorithms to compute them. First, events were predicted by the multi-parameter model and a windowing algorithm was used to modify breath-by-breath events into events similar to those scored manually (e.g. 10 second events, etc.). The RDI was calculated by summing the events and dividing by "valid study time" (note: not sleep time). The epoch-by-epoch confusion matrices were computed by summing the predicted and scored events per 30 second epoch. Diagnostic agreement was also computed based on the ability of the system to accurately predict a range of RDIs (more information in the Results section). Some subtleties exist in these statistics. For instance, high RDI patients will have 1000s of events whereas low RDI patients will have 10s of events. The high RDI patients will therefore dominate the epoch-by-epoch Kappa value.

An important feature of our multi-parameter modelling is the addition of temporal information. Many of the parameters are highly predictive of events, but have a high rate of false positives as well. When analyzing the data however, it is clear that events have a different temporal structure (smooth) than the false alarms (peaky). In addition, some parameters detect events, some parameters predict recovery (or post-events), and some parameters indicate normal breathing. By utilizing a temporal model, additional information about the progression of the signals over time can be utilized to make decisions.

There are many approaches to adding temporal information. The most common approach is averaging which is a subset of moving average filters (finite impulse response filters, or FIRS). Strict averaging multiplies each sample by 1/N (where N is the number of samples in the average) and sums the results. Moving average or FIR filters are similar, except that each sample can have a different weight. This allows the filter to give varying emphasis to different delays or time frames (for instance, more emphasis to the recent past than the distant past). Implementation of this type of filter often includes the concept of a tap-delay line which is a memory structure that stores the recent past of the signal and scales each one to create the model output. We call this approach the TDL (tap-delay line) and use it as our baseline temporal filtering approach.

We also experimented with temporal neural network models and the Hidden Markov Model (HMM). We utilized a tap-delay neural network (TDNN) model which is the most common temporal neural network and is a non-linear generalization of the FIR filter. The HMM provides a state-based (stochastic) approach to extracting temporal information. The HMM creates states based on the inputs to the model and calculates the likelihood that the current set of data was generated by the model. Therefore, an HMM model would be created with apnea events and the data leading up to and following the event. Other HMM models would be created to represent other events or normal breathing. New data is passed through all the models and the model that has the highest probability of matching the data "labels" the data.

In this study, with only 20 patients in the training set, the TDL, TDNN, and HMM models all produced roughly equivalent performance. In modeling theory, the simplest model that has adequate performance is most likely to generalize across new data, particularly with a small training set (increased complexity requires larger training sets to adequately train). For this reason, our analysis focused on the TDL model. Experimentally, 5 memory elements were sufficient to capture the information of interest in the signal. Typically, this memory was centered on the breath of interest, meaning that the memory structure contained the breath under test and the 2 breaths before and after it.

Miscellaneous Analysis

Several side-studies were implemented during the project.

Arousal Detection

One such study looked at the ability of the parameters to determine arousals. In our database, 72% of events have a labeled arousal within 5 seconds after the event. The majority of the remaining 28% appear to have similar characteristics to an arousal in the breathing parameters, but are not labeled as arousals (insufficient EEG activity?). In a quick evaluation of our parameters, we were able to detect these arousals using only DC drop with an AUC of 0.85.

Analysis of Saturation Differences

Another topic of interest was whether the saturation information at the central site was similar in value and discriminability to the saturation at the finger. The three studies were scored, first with the finger saturation and a month later with the nasal alar saturation. The scoring is shown in the table below. We also calculated the epoch-by-epoch confusion matrix and determined that the Kappa statistic for this matrix was 0.92 and had an agreement rate of 98%. The differences in the scoring are similar to if not less than the typical difference in scoring between multiple scorers, and thus considered insignificant.

|  | Finger SpO2 | Alar SpO2 |
|---|---|---|
| SPOC-04 | 36.5 | 36.1 |
| SPOC-06 | 29.1 | 25.2 |
| SPOC-08 | 13.9 | 12.2 |

|  |  | Nasal Alar | | |
|---|---|---|---|---|
|  |  | 0 | 1 | 2 |
| Finger | 0 | 2368 | 9 | 0 |
|  | 1 | 51 | 420 | 0 |
|  | 2 | 0 | 0 | 7 |

Next, we evaluated the differences in our models when nasal saturation was replaced by finger saturation. Some caveats of note are that the NICO (alar) reports saturation in increments of 1% whereas the Alice system (finger) reports saturation in increments of 0.1%. When looking for saturation drops of 2-5%, the increased resolution of the Alice system is particularly important. Additionally, the NICO does not seem to handle the increased signal strength of the ear-lobe sensor when attached to the alar. The alar has less flesh and more blood flow than the finger, thus producing a much stronger signal. In our previous studies using the Novametrix Oxypleth, we did not have this problem. The NICO tended to threshold the saturation at 100% and thus produced even less resolution than the finger. It is important to note that this is a data collection limitation, not a physiologic limitation. The following table shows the percent of the time that the saturation at the nasal alar was determined to be 100% (relatively uncommon normally).

| Patient | Total Clipped Time (hrs) | Total Record Time (hrs) | % Time Clipped |
|---|---|---|---|
| SPOC-01 | 3.58 | 8.75 | 40.9% |
| SPOC-02 | 5.69 | 8.77 | 64.8% |
| SPOC-03 | 2.85 | 3.37 | 84.4% |
| SPOC-04 | 0.27 | 7.40 | 3.7% |
| SPOC-05 | 0.00 | 6.76 | 0.0% |
| SPOC-06 | 0.35 | 7.80 | 4.5% |
| SPOC-07 | 1.64 | 6.62 | 24.8% |
| SPOC-08 | 0.26 | 8.79 | 3.0% |
| SPOC-09 | 0.42 | 7.21 | 5.8% |
| SPOC-10 | 0.73 | 6.06 | 12.1% |
| SPOC-11 | 0.02 | 7.70 | 0.2% |
| SPOC-12 | 7.64 | 7.83 | 97.7% |
| SPOC-13 | 4.35 | 7.53 | 57.8% |
| SPOC-14 | 3.40 | 7.85 | 43.3% |
| SPOC-16 | 1.14 | 7.86 | 14.5% |
| SPOC-17 | 0.09 | 7.20 | 1.2% |
| SPOC-18 | 0.01 | 6.91 | 0.1% |
| SPOC-19 | 4.81 | 7.34 | 65.6% |
| SPOC-20 | 0.02 | 6.40 | 0.3% |
| SPOC-21 | 0.01 | 6.23 | 0.2% |
| SPOC-22 | 2.93 | 7.79 | 37.6% |
| SPOC-23 | 4.77 | 7.96 | 59.9% |
| SPOC-24 | 1.01 | 5.34 | 18.9% |
| SPOC-25 | 0.00 | 7.13 | 0.0% |
| SPOC-26 | 0.07 | 2.96 | 2.3% |
| SPOC-27 | 2.76 | 7.07 | 39.0% |
| SPOC-28 | 1.37 | 8.49 | 16.2% |
| SPOC-29 | 0.32 | 6.52 | 4.9% |
| SPOC-30 | 1.00 | 6.43 | 15.5% |
| SPOC-31 | 1.28 | 6.64 | 19.2% |
| SPOC-33 | 0.06 | 6.63 | 0.9% |
| SPOC-34 | 0.07 | 7.56 | 0.9% |
| SPOC-35 | 0.71 | 7.35 | 9.6% |
| SPOC-36 | 0.94 | 5.20 | 18.1% |
| SPOC-37 | 3.14 | 7.26 | 43.3% |

When comparing nasal alar saturation and finger saturation, we found that the average saturation drop during events with the nasal alar was 2.5±1.8 and with the finger 2.8±2.1. When analyzing the delays in the signals by calculating the optimal time-shift to align the saturation drop with the event window, the finger saturation delay was 7.5 seconds and the nasal alar delay was 5 seconds. Theoretically, central sites may desaturate faster than peripheral sites, although this cannot be strictly proved with this data due to differences in the data acquisition of the finger (Alice) and alar (NICO). Lastly, we calculated the ROC curves for detection of events with the nasal and finger saturation. FIG. 9(b) shows that these two ROC curves are virtually identical. Thus, although the saturation signals were collected differently and were suboptimal at the nasal alar, the information content of both signals was equivalent. Oxygen Desaturation Index To further analyze the differences in saturation, and also create baseline model statistics, we endeavored to automatically calculate the manual scoring oxygenation desaturation indices (ODIs) from the PSG and PPG data. In the patient reports, the Desat Index is simply given as "#/hr", with no further explanation of how it is calculated. We assumed they used a 3% cutoff to get the number of Desats (#) and that they divided by Time in Bed (TIB), but we don't know if these assumptions are correct.

For our calculations, the Desaturation Index is equal to the number of times the $SpO_2$ value falls below a cutoff value (relative to a baseline) divided by the time in bed (TIB). For both the predicted alar-based (PPG) and finger-based (PSG) desaturation indices, we evaluated a variety of $SpO_2$ cutoff values to determine which one most closely matched the manually scored Desaturation Index as well as dividing by both TIB and total sleep time (TST). The TIB is the time from Light Off to Light On and TIB is equal to the TST plus the times labeled WK. We optimized these parameters by minimizing the mean squared error (MSE) between the predicted ODI and the manually scored ODI. It turns out that using the PSG $SpO_2$ to predict scoring (optimal possible solution), a cutoff of 3.5% and TIB gave the lowest MSE. Except for 3 patients, the difference between Total Recording time and TIB is less than 30 minutes.

From this optimization, we calculated 3 sets of Desat Indices:

Using the PSG signal, we calculated Desat Index=# of Desats/TIB (Column C) using a cutoff of 3.5%.
Using the PPG signal, we calculated Desat Index=# of Desats/TIB (Column D) using a cutoff of 3.01%.
Using the PPG signal, we calculated Desat Index=# Desats/Total Recording Time (Column E) using a cutoff of 3.01%.

The results are shown in the table below. We also calculated the mean squared error without patients 16 and 18. Because these two patients have large Desat Index values, they also have larger absolute error values and have a disproportionate effect on the MSE value ($L_2$ and high norms emphasize larger errors more than smaller errors). We thought it would be helpful to look at the MSE without these two patients included. The table shows MSE with and without those two patients.

| Column A Patient (SPOC)# | Column B Given Desat Index (PSG) | Column C Calculated Desat Index PSG cutoff = 3.5%/TIB | Column D Calculated Desat Index PSG cutoff = 3.01%/TIB | Column E Calculated Desat Index PSG cutoff = 3.01%/Rectime |
|---|---|---|---|---|
| 1 | 7.4 | 7.3 | 9.0 | 9.2 |
| 2 | 3.6 | 7.2 | 4.0 | 4.2 |
| 3 | 4.7 | 2.4 | 0.9 | 0.9 |
| 4 | 14.5 | 15.6 | 15.8 | 15.5 |
| 6 | 17.9 | 20.5 | 15.9 | 16.5 |
| 8 | 7.4 | 10.4 | 7.8 | 7.5 |
| 9 | 8.9 | 6.4 | 15.5 | 15.1 |
| 11 | 1.3 | 0.0 | 0.0 | 3.8 |
| 12 | 0.1 | 0.2 | 0.0 | 0.0 |
| 13 | 7.1 | 7.1 | 5.2 | 5.0 |
| 14 | 10.1 | 9.0 | 8.9 | 8.6 |
| 16 | 94.1 | 88.0 | 80.1 | 77.1 |
| 17 | 0.6 | 2.2 | 1.6 | 1.5 |
| 18 | 39.8 | 42.1 | 33.8 | 31.4 |
| 19 | 5.1 | 3.5 | 1.0 | 0.9 |
| 20 | 20.2 | 14.8 | 14.8 | 13.9 |
| 21 | 2.0 | 7.0 | 6.2 | 3.5 |
| Mean Std. | 14.4 | 14.3 | 13.0 | 12.6 |
| Dev. | 22.7 | 21.5 | 19.3 | 18.4 |
| MSE* MSE: | 0 | 8.6 | 21.8 | 29.0 |
| no 16&18** | 0 | 7.0 | 9.2 | 8.8 |

*MSE: Mean Squared Error between values in column and Given Desat Index (Column B)
**MSE no 16&18: Mean Square Error not including patients 16 and 18 (patients with very high index values)

FIG. 10 shows the excellent correlation between the ODI calculated with the nasal probe and the ODI calculated with the finger probe. The correlation coefficient is 0.987 and the bias is 0.7 with a precision of 2.

Classification of Central Vs. Obstructive Apnea

We also implemented a short study to determine the ability of the current SPOC data to predict the difference between central and obstructive apneas. In particular, we studied the EPISPOC patients since the epiglottal catheter allows for more "scientific" scoring of obstructive, central, and mixed apneas. At the time this study was done, 4 EPISPOC patients were available (102-105). The study utilized a new parameter called BR Energy to classify. BR Energy estimates the breath effort by summing the energy (square of BR signal) over a 10-second window and dividing by the average energy over a 300-second baseline window. This methodology determines changes in breathing effort. The tables below summarize the performance of the model to detect the difference between central and obstructive apnea and also the difference between central and mixed versus obstructive apnea. Agreement rates are good and the Kappa statistic indicates "moderate agreement" between the PSG and predicted labeling.

| | | Central vs. CE System | |
|---|---|---|---|
| | | Central | Obst |
| PSG | Central | 40 | 39 |
| | Obst | 28 | 465 |
| PSG | Central | 7.0% | 6.8% |
| | Obst | 4.9% | 81.3% |

Kappa = 0.48,
Agreement = 88%

| Central and Mixed vs. Obstructive | | | |
|---|---|---|---|
| | | CE System | |
| | | Cen/Mix | Obst |
| PSG | Cen/Mix | 256 | 94 |
| | Obst | 135 | 358 |
| PSG | Central | 30.4% | 11.2% |
| | Obst | 16.0% | 42.5% |

Kappa = 0.48,
Agreement =

The Model and Training Set Analysis

The final SPOC model evolved over time, to include the following parameters:

Nasal pressure drop: for each breath, the percent change in amplitude from baseline is computed. The signal is filtered to remove high-frequency spikes and outliers, and the nasal pressure drop is computed as the difference between the baseline peak amplitude minus the maximum peak amplitude during the breath. For stable breathing, the baseline peak amplitude is the average of peak amplitude over a 40-breath window centered on the breath of interest. For unstable breathing (e.g. during periods of many events), the baseline peak amplitude is the mean of the largest 50% of the peaks in that window.

$SpO_2$ drop: for each breath, $SpO_2$ Drop is computed as the mean of the $SpO_2$ during that breath subtracted from baseline. The baseline $SpO_2$ is calculated as the modified median of the $SpO_2$ in the two minute window centered on the current breath, where the modified median is the $80^{th}$ percentile value of the sorted breaths in that window.

Pleth DC drop area: for each breath, DC Drop Area is the integral of the portion of the DC signal that drops 1% or more below the baseline. The AC and DC signals are separated using the patented algorithm to optimally separate the cardiac signals from the respiratory and other signals. The baseline is computed as the average of the DC signal in a five-minute window centered on the breath of interest.

Pleth heart rate: for each breath, the pleth cardiac signal is parsed for peaks and the heart rate is determined by counting the peaks in the preceding 10 seconds.

Each of these parameters is time shifted (when necessary) and weighted using a five-tap delay line (TDL model) to create a single signal that indicates events. An optimal threshold is then determined to detect events. The events are then utilized to calculate RDI, the epoch-by-epoch Kappa statistic, and diagnostic agreement.

Figure 11:
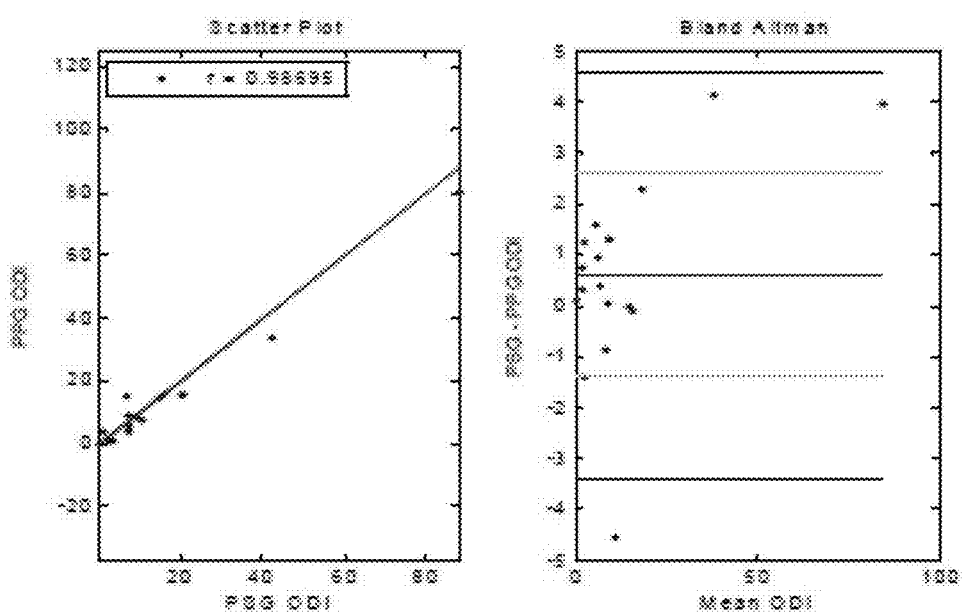
FIG. 11 shows correlation and Bland Altman for nasal (PPG) vs. finger (PSG) ODI
Figure 12:
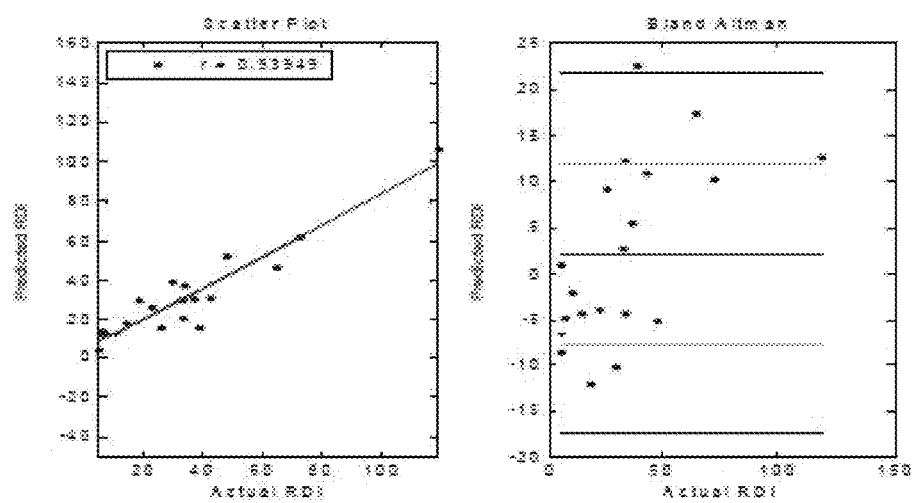
FIG. 12 shows correlation between SPOC model and scored RDI
Figures 13A, 13B:
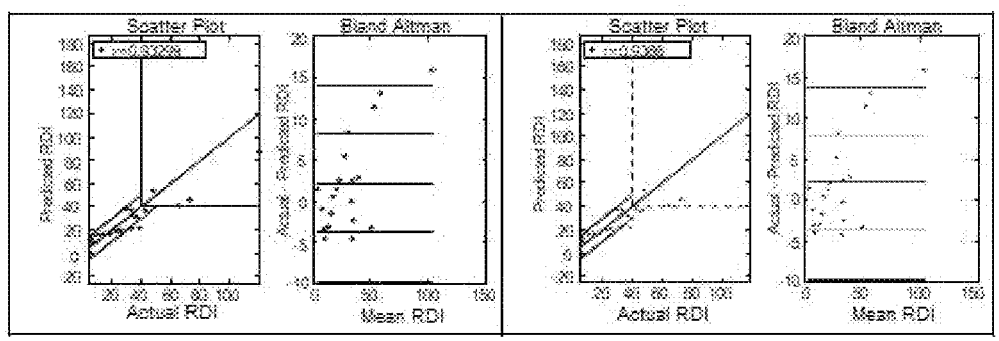
FIG. 13 shows leave-one-out performance for final model, (a) Correlation of predicted versus actual RDI using leave-one out performance. r=0.933; (b) Correlation of predicted versus actual RDI using all 15 patients in training set. r=0.937.
Figure 14:
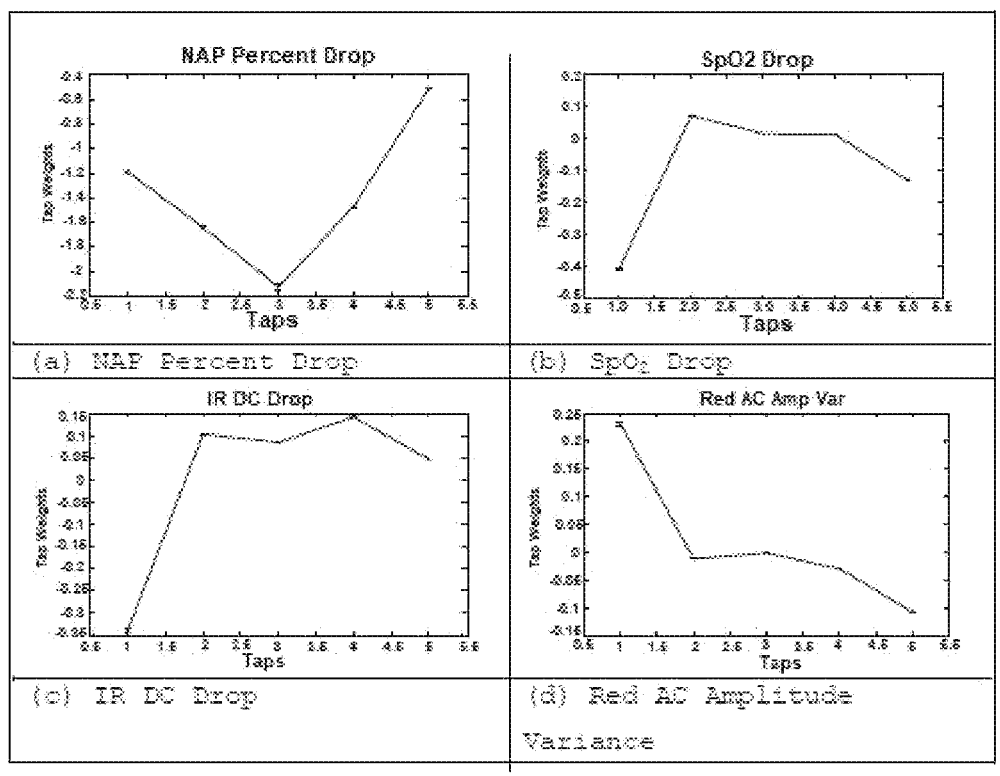
FIG. 14 shows amplitude and variance of weights derived from leave-five-out analysis.
Figure 15:
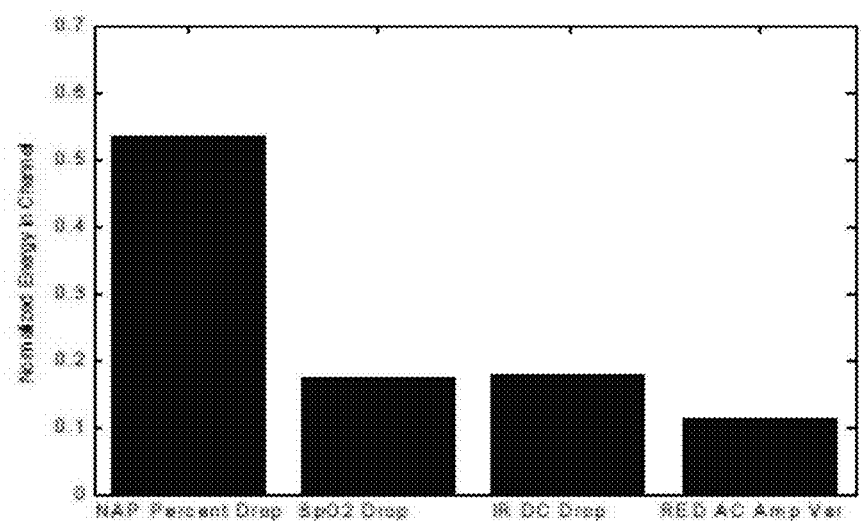
FIG. 15 shows the contribution of each channel to the model's output.
Figures 16A, 16B:
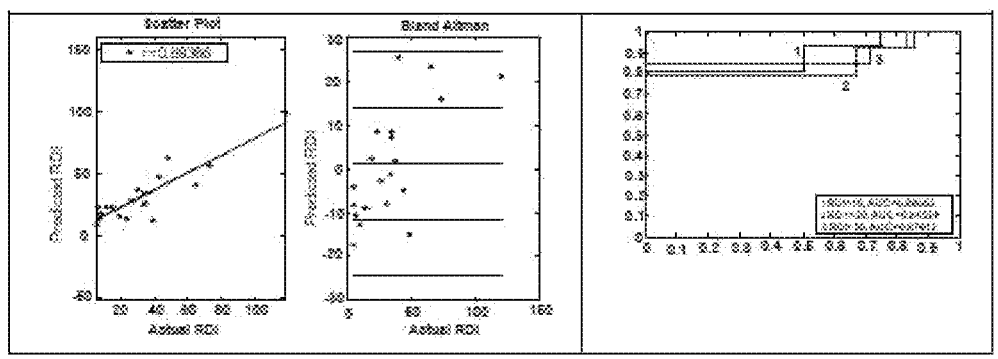
FIG. 16 shows the performance of a pleth-only model: (a) Correlation plot and Bland Altman; (b) ROC curves for RDI>10, 20, 30
Figure 17:
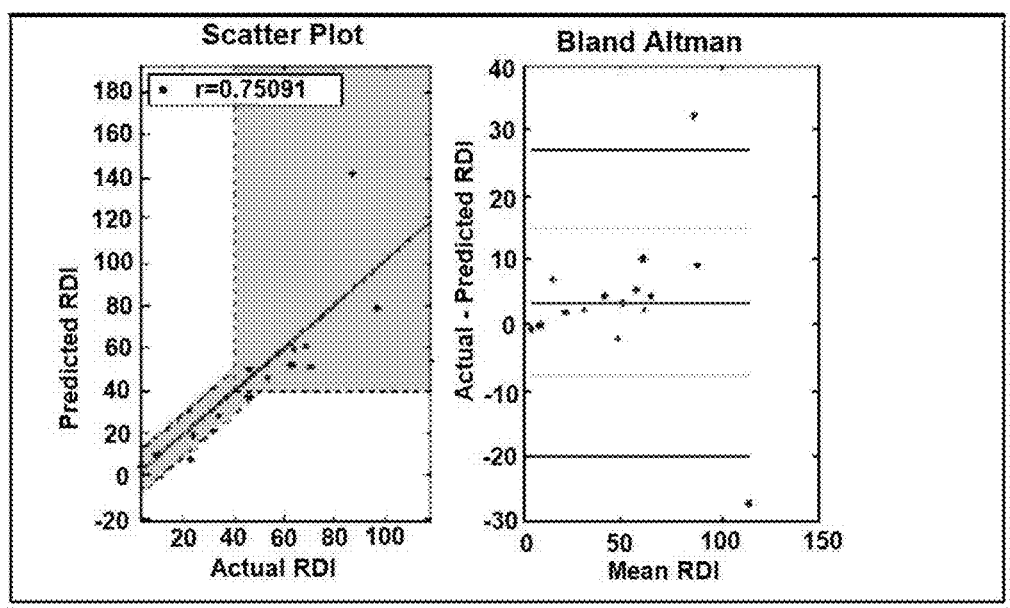
FIG. 17 shows an Example of diagnostic agreement in correlation plot.

Performance of this model was good as shown in FIG. 11; it is noted that the models must be scaled to correlate well with RDI, rather than actually determining the actual value of RDI. The model may be improved through evaluation of robustness and routine experimentation. We not only created a new model that matched RDI without scaling, we also did a series of tests on the models to determine their "robustness" and ability to generalize outside of the training set. The resulting new model performs well on mean RDI error (mean absolute error of 8.9, dominated by the large RDI patients), diagnostic agreement (95%), and the Kappa statistic of the confusion matrix (0.465). The new model replaced the "Pleth DC Drop Area" parameter with the similar "Pleth IR DC Drop" parameter and replaced the "Pleth heart rate" parameter with the "Pleth Red AC Amplitude Variance" parameter.

Pleth IR DC Drop: for each breath, the IR DC Drop is calculated as the ratio between the average IR DC value during the breath and the baseline IR DC value. The baseline IR DC value is an average of the IR DC value over a 40-second window centered on the current breath.

Pleth Red AC Amplitude Variance: for each breath, the Pleth Red AC Amplitude Variance is calculated as the variance of the peak-to-trough distances of all beats detected in the breath and 10 seconds prior to the breath.

Figure 18:
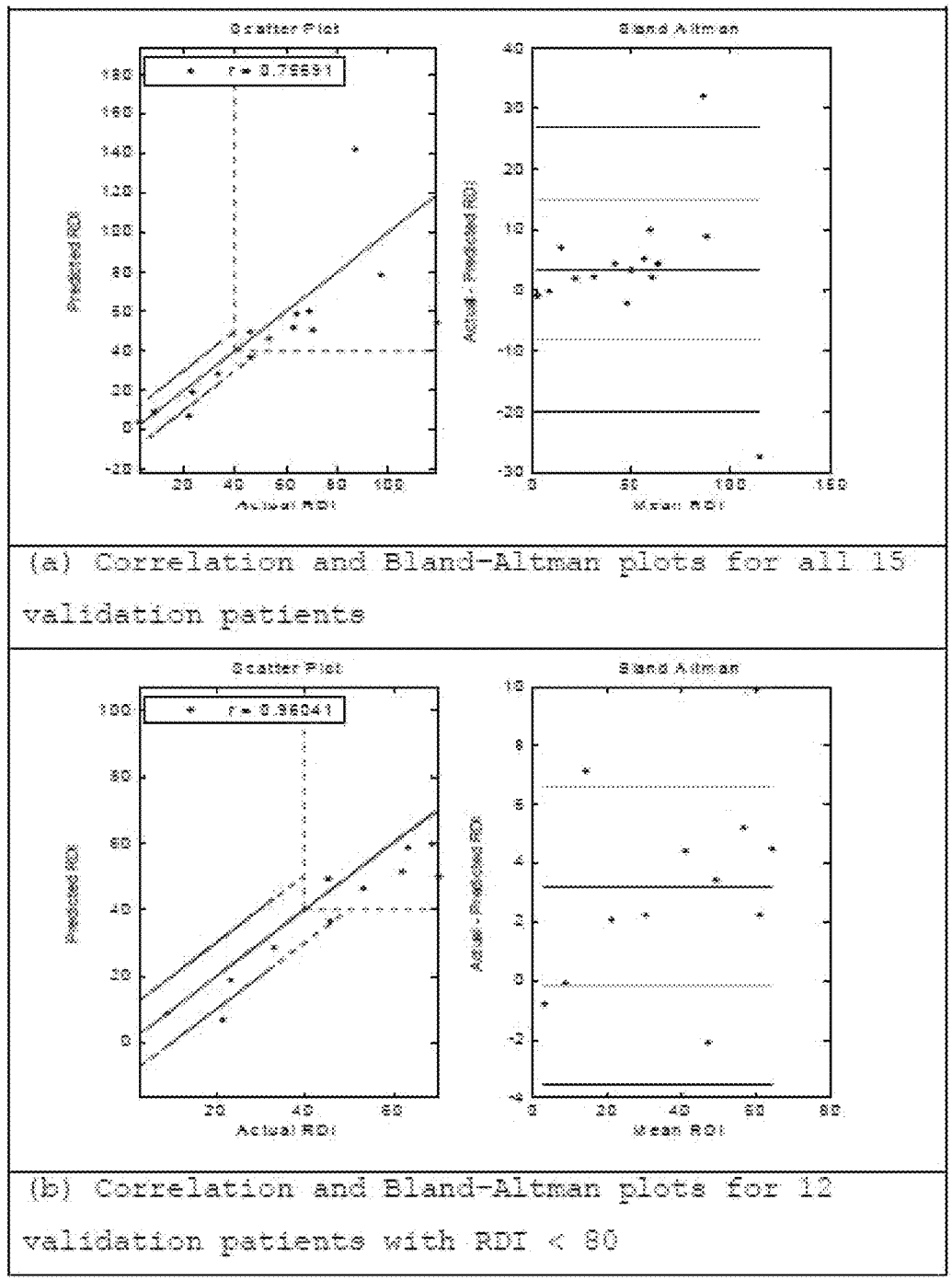
FIG. 18 shows validation results for the SPOC model: (a) Correlation and Bland-Altman plots for all 15 validation patients; (b) Correlation and Bland-Altman plots for 12 validation patients with RDI<80.

Model robustness was evaluated using the leave-one-out and leave-five-out techniques. In the leave-one-out method, 15 different models were created with only 14 of the 15 patients with RDI<40. Each model was used to only predict the RDI for the one patient not included in the training set. The final evaluation is determined by calculating statistics for the 15 different models on each of the "left out" patients. As shown in FIG. 18, performance of the model during the leave-one-out testing was nearly identical to the performance of the model using all 15 patients as the training and testing sets. This indicates that the model is robust across all 15 patients used in this study.

Figure 19:
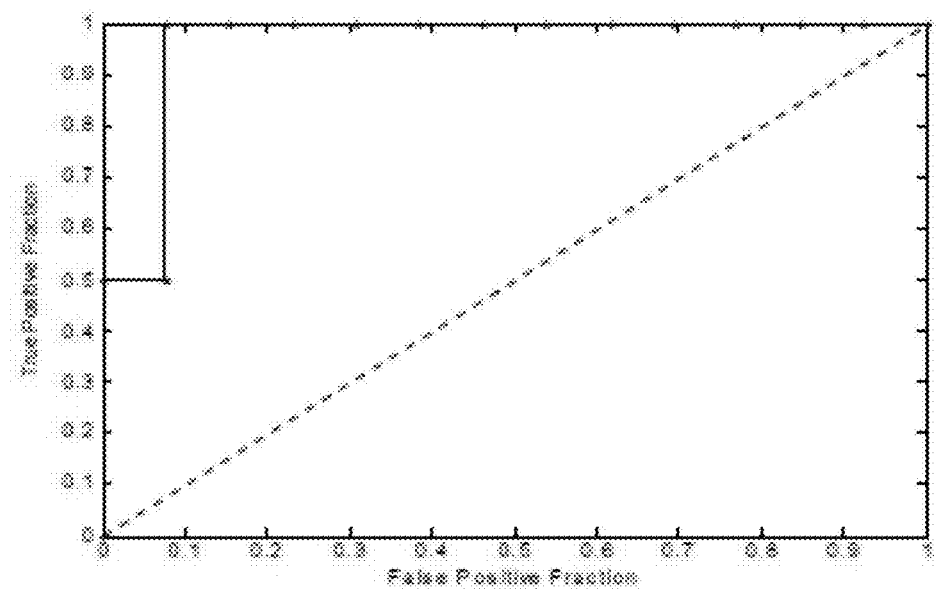
FIG. 19 shows ROC curve for validation set. All three curves, RDI>10, 15, and 20 are identical.

To further test the robustness of this new model, we implemented a leave-five-out methodology that utilizes only 10 patient databases for training. This is a more difficult task since the training set is smaller. Performance was similar to above again proving successful generalization. We also analyzed the variance of the weights in the model. A good model will have very similar weights when trained on different data sets—this indicates that the model is not sensitive to the choice of training set and is capturing the information of interest. FIG. 19 shows the weights for each of the 5 taps of the TDL for each parameter in the final model. In particular, notice the variance bars for each weight and how small the variance is between the 50 random selections of 10 patients. This is an excellent indication that the models are robust to patient selection.

Our last sanity check to ensure we have a robust model is to utilize the EPISPOC patients as an independent test set. Using the 15 patients with RDI<40 as the training set and the 4 good EPISPOC patients as the test set, we achieved a correlation coefficient of 0.99 and a 100% diagnostic agreement. The table below shows the predicted and actual RDIs for these patients.

| | PSG RDI | SPOC RDI |
|---|---|---|
| EPISPOC-102 | 48.4 | 53.2 |
| EPISPOC-103 | 42.2 | 51.1 |
| EPISPOC-104 | 70.2 | 75.9 |
| EPISPOC-105 | 47.5 | 53.6 |

In summary, all indications are that this model should generalize well to new data, under the following assumptions: (1) The training data represents the population of interest well, and (2) the test data comes from the same population as the training data.

Further Model Evaluation

Figure 20:
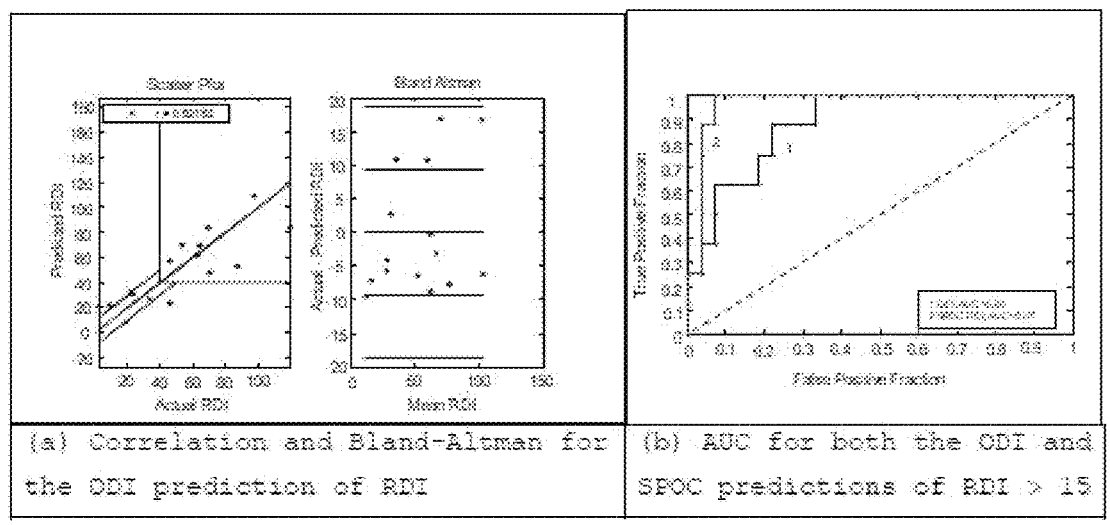
FIG. 20 shows the performance of ODI model of RDI: (a) Correlation and Bland-Altman for the ODI prediction of RDI; (b) AUC for both the ODI and SPOC predictions of RDI>15.

It is desirable to understand the amount of information from each parameter that is utilized by the model. To do this, the energy in each of the four channels was summed across the 20 patients and the four parameters were then normalized to sum to 1. FIG. 20 shows the contribution from each channel in the model's output. As expected, nasal pressure has the largest single contribution to the model at ~50%, with the other three parameters contributing between 10% and 18%.

Further analysis shows that the largest errors in the prediction of the RDI arise from patients who have a significant difference between sleep time and study time. The table below shows that the two patients who fell outside the White/Westbrook diagnostic agreement both had significant wake times during the study. The current SPOC model does not have the capability to compute sleep time and therefore assumes the patient is asleep during the entire study.

|  | PSG RDI | SPOC RDI | TST Over-Prediction (hrs) |
|---|---|---|---|
| SPOC-01 | 33.2 | 21.8 | 4.3 |
| SPOC-02 | 10.2 | 14.9 | 0.9 |
| SPOC-03 | 18 | 16.1 | −1.6 |
| SPOC-04 | 36.5 | 33.1 | 2.3 |
| SPOC-05 | 5.3 | 11.6 | 2.3 |
| SPOC-06 | 29.1 | 38.1 | 1.1 |
| SPOC-07 | 25.2 | 20.9 | 1.0 |
| SPOC-08 | 13.9 | 17.1 | 1.2 |
| SPOC-09 | 32.6 | 36.0 | 1.2 |
| SPOC-10 | 47.5 | 53.0 | 0.3 |
| SPOC-11 | 5.5 | 13.4 | 0.9 |
| SPOC-12 | 4.8 | 1.6 | 2.8 |
| SPOC-13 | 33.3 | 34.4 | 1.5 |
| SPOC-14 | 42.4 | 37.9 | 1.5 |
| SPOC-16 | 119 | 92.1 | 0.5 |
| SPOC-17 | 6.9 | 9.7 | 0.6 |
| SPOC-18 | 72.1 | 49.1 | 1.0 |
| SPOC-19 | 22.2 | 21.3 | 0.6 |
| SPOC-20 | 64.3 | 43.3 | 2.0 |
| SPOC-21 | 38.3 | 22.1 | 3.6 |

* RED Patients fell outside White/Westbrook Agreement Boundaries

Pleth Only Model

Since the Nasal Pressure is the major contributor to the model, we decided to evaluate the performance of a pleth only model (e.g. using data only from the pulse-oximeter). The best model parameters were:

$SpO_2$ Drop: discussed earlier

IR BE Energy: Breath effort signal as defined in the obstructive/central apnea section.

RED DC Drop Area: The area of the DC drop in the RED signal relative to a baseline. The baseline is as computed in the same way as in previous similar parameters.

Pleth Red AC HR Variability: the variability of heart rate measured in a 10 second window preceding the current breath.

Figure 21:
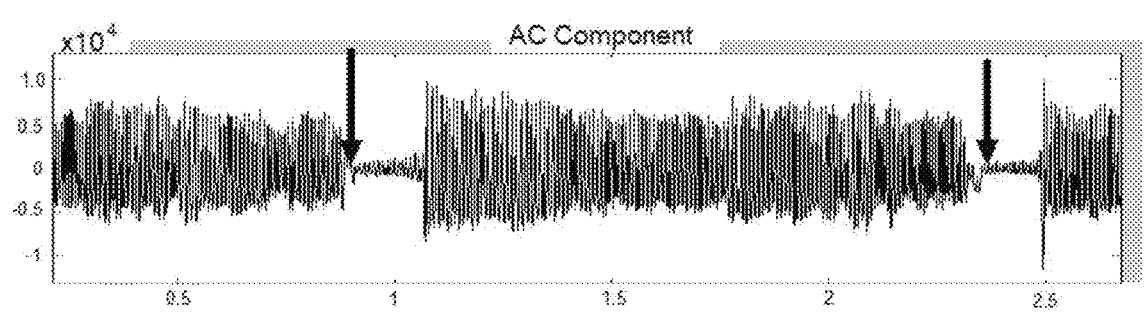
FIG. 21 provides the PCC of a PPG signal from a sensor placed on the right cheek. The carotid artery is briefly occluded (arrows) and the amplitude of the signal is dramatically decreased indicating diminished facial blood flow.

This model performed well, but not as well as the model that also included nasal pressure. FIG. 21(a) shows the correlation plot for RDI with a correlation coefficient of 0.894, with a bias of approximately 1 RDI point and precision of approximately 10. The ROC curves showed an AUC between 0.84 and 0.89 for the RDI>10, 20, predictions.

Statistical Analysis Techniques

This section will summarize the rules and techniques we used to calculate the various statistics used during this project.

Sensitivity Analysis

For sensitivity analysis, events needed to be matched between the manual and predicted scoring. This matching then results in the labeling of events as true positive, false positive, and false negative (true negatives are ill-defined). The following rules (consistent with those used in De Almeida, et. al. "Nasal pressure recordings to detect obstructive sleep apnea", Sleep Breath 2006 10(2):62-69) were applied for aligning and matching events:

The time at the center of each event, both manually scored and predicted, was used for alignment.

If a predicted event occurred within 10 seconds of an actual event, it was scored a true positive.

False negative events were those that were manually scored as an event without a predicted event within 10 seconds.

False positive events are when a predicted event was not within 10 seconds of a manually scored event.

If two predicted events occurred within 10 seconds of an actual event, one was scored a true positive, the other a false positive.

White/Westbrook Diagnostic Agreement

As defined in "D. White, T Gibb, J Wall, P Westbrook, 'Assessment of Accuracy and Analysis Time of a Novel Device to Monitor Sleep and Breathing in the Home', Sleep, 18(2):115-126", the diagnostic agreement rules are as follows:

Agreement defined as:
AHI≥40 events per hour (e/hr) on both systems
If AHI<40 on PSG, AHI within 10 e/hr on both
Overestimate of AHI defined as:
AHI 10 e/hr greater on system than PSG (both <40 e/hr)
Underestimate of AHI defined as:
AHI 10 e/hr less on system than PSG (both <40 e/hr)

Figure 22:
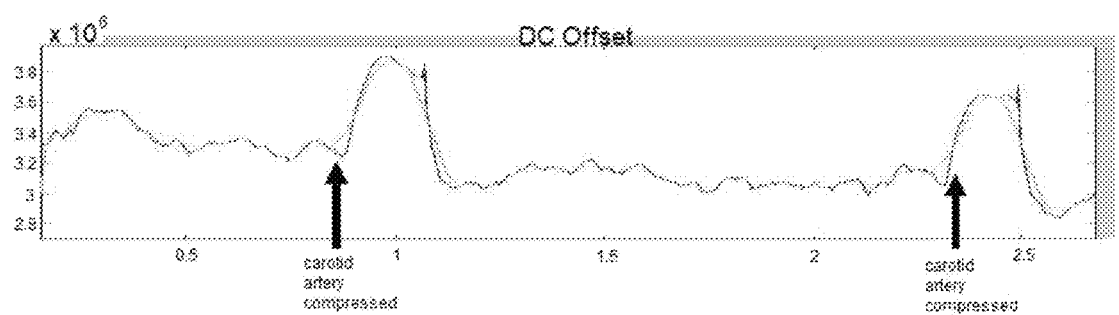
FIG. 22 shows the LFC of the same PPG signal demonstrating diminished venous capacitance (arrows) in an upright subject due to decreased venous blood when the carotid artery is compressed (decreased capacitance increases light transmission through the vascular bed).

The most recent correlation plots show the diagnostic agreement regions with dashed lines. FIG. 22 shows the diagnostic agreement region in grey. In the example plot, only 1 of the data points falls outside the diagnostic agreement range.

Kappa Agreement

Cohen's Kappa statistic provides the degree to which two judges concur in the respective classification of N items into k mutually exclusive categories—relative to that expected by chance. It is a "chance corrected proportional agreement". Unweighted Kappa assumes no relationship between events, Linear weighted Kappa assumes numeric relationship (e.g. 1 is closer to 2 than it is to 3). An example epoch-by-epoch confusion matrix of a system prediction that has 90% agreement (always predicts zero events per epoch) is shown below. As expected, the Kappa value for this matrix is 0. To the right of the matrix is a set of generally accepted interpretations of the ranges of Kappa values.

|  |  | System Prediction | | | |
|---|---|---|---|---|---|
|  |  | 0 | 1 | 2 | 3 |
| PSG | 0 | 8154 | 0 | 0 | 0 |
|  | 1 | 870 | 0 | 0 | 0 |
|  | 2 | 9 | 0 | 0 | 0 |

| kappa | Interpretation |
|---|---|
| <0 | No agreement |
| 0.0-0.19 | Poor agreement |
| 0.20-0.39 | Fair agreement |
| 0.40-0.59 | Moderate agreement |
| 0.60-0.79 | Substantial agreement |
| 0.80-1.00 | Almost perfect agreement |

Agreement Percent = 90.3%
Kappa = 0!

Validation Set Results

The validation set consists of 15 patients. We ran an analysis of the SPOC data from this validation set and developed predictions of RDI and events. At this point, scoring information on the patients was utilized to fully analyze the results.

The patient population in the validation set was more severe than in the training set. The mean RDI for the training set was 33 with 20% of the patients having an RDI>40, while the mean RDI for the validation set was 53 with 60% of the patients having an RDI>40. The scored RDI and the predicted RDI for each patient are shown below.

| SPOC RDI | RDI from Alice PSG Scoring Report |
|---|---|
| 3.9 | 2.4 |
| 8.8 | 8.6 |
| 7.2 | 21.5 |
| 18.9 | 23.1 |
| 28.6 | 33.1 |
| 49.6 | 45.4 |
| 36.9 | 45.7 |
| 46.3 | 53.2 |
| 51.7 | 62.1 |
| 58.9 | 63.4 |
| 59.8 | 68.8 |
| 50.2 | 70.1 |
| 141.8 | 87.1 |
| 78.8 | 96.8 |
| 54.5 | 118.6 |

Although the population was somewhat different than the training set, the SPOC algorithms still performed quite well. The system correctly classified all severe (RDI>40) patients as severe. Although the RDI correlation is lower than in the training set, this was driven by two outliers with high RDI values (RDI>80). As shown in FIG. 23 the correlation coefficient for all 15 patients was 0.76 (bias=3, precision=10), while the correlation coefficient for patients with RDI<80 is 0.96 with a bias of 3 and precision of 3. The plots also show a diagnostic agreement of 93% missing only on SPOC-22 where the predicted value was 7 and the scored RDI was 20.

The table below shows the epoch-by-epoch analysis of the number of events. The Kappa statistic for the validation set was 0.47 which is slightly higher than the training set.

|  |  | System Number of Events | | | |
|---|---|---|---|---|---|
|  |  | 0 | 1 | 2 | 3 |
| PSG System | 0 | 7064 | 1364 | 31 | 0 |
| Number of | 1 | 961 | 1969 | 18 | 1 |
|  | 2 | 34 | 61 | 3 | 0 |

With only 2 patients in the validation set having an RDI <20 and both of them being less than 10, the ROC curves and AUC for RDI>10, 15, and 20 were all identical. The AUC was excellent at 0.96. The ROC for all three are shown in FIG. 24.

As discussed above with the AUCs for various RDIs, the AUC analysis with ODI in the validation set is of questionable validity due to the fact that only 2 patients have RDIs less than 20. The table of ODIs versus PSG RDIs is shown below.

| SPOC ODI | PSG RDI |
|---|---|
| 0.00 | 2.40 |
| 0.93 | 8.60 |
| 6.95 | 21.50 |
| 5.96 | 23.10 |
| 3.87 | 33.10 |
| 21.79 | 45.40 |
| 1.66 | 45.70 |
| 29.22 | 53.20 |
| 24.33 | 62.10 |
| 28.55 | 63.40 |
| 37.21 | 68.80 |
| 16.08 | 70.10 |
| 18.92 | 87.10 |
| 51.87 | 96.80 |
| 37.67 | 118.60 |

The correlation plot for ODI prediction of RDI (after linear scaling) are shown in FIG. 24. The correlation coefficient is only r=0.82 and the precision is 10 (after linear adjustment, the bias is 0 by definition). The ROC curves using both RDI and SPOC prediction for RDI>15 on all 35 patients (to get a better distribution of low RDI patients) is shown in FIG. 25. Notice that the SPOC RDI has an AUC of 0.97 whereas the ODI AUC is 0.88.

Review of Outliers

In the validation set, there were 3 patients we considered to be outliers: SPOC-22, SPOC-24, and SPOC-26 (although SPOC-24 and SPOC-26 were correctly classified as "severe"). The table of predicted versus manually scored RDIs in the validation set is shown below, with the outliers highlighted.

| Patient | PSG RDI | Reported SPOC RDI |
|---|---|---|
| SPOC-22 | 21.5 | 7.2 |
| SPOC-23 | 70.1 | 50.2 |
| SPOC-24 | 118.6 | 54.5 |
| SPOC-25 | 68.8 | 59.8 |
| SPOC-26 | 87.1 | 141.8 |
| SPOC-27 | 45.7 | 36.9 |
| SPOC-28 | 8.6 | 8.8 |
| SPOC-29 | 53.2 | 46.3 |
| SPOC-30 | 33.1 | 28.6 |
| SPOC-31 | 45.4 | 49.6 |
| SPOC-33 | 62.1 | 51.7 |
| SPOC-34 | 96.8 | 78.8 |
| SPOC-35 | 23.1 | 18.9 |
| SPOC-36 | 63.4 | 58.9 |
| SPOC-37 | 2.4 | 3.9 |

In our preliminary report of validation set results, we under predicted RDI for two of these (22 and 24) and over-predicted the RDI of SPOC-26. A closer look at SPOC-26 showed that there were four hours of time in which the pleth signal was "disconnected". This type of error was not being detected by our algorithm at the time of testing. After correcting for this disconnection, however, the RDI estimate for SPOC-26 drops from 141 to 52 (although there were some disconnections in the other patients, none were long enough to significantly affect the scoring).

In analyzing the under-prediction that is prevalent for the high RDI patients, there appears to be two primary causes: (1) the SPOC system was trained on low and moderate patients in order to produce better diagnostic accuracy, and (2) there was a significant difference between sleep time and study time in a few patients.

In our models, a good example of how training on low and moderate patients affects the scoring of the severe patients is in calculating the baseline. Each parameter (such as DC Drop and SpO$_2$ Drop) calculates a "baseline" from which to compare the current breath. For patients with many events, this baseline is artificially more "severe" on average, which causes the current breath to seem less "severe" and allows a number of events to just miss their "threshold". As described previously, in the Nasal Pressure Drop parameter we utilized two separate baseline calculations—one for moderate and mild patients and one for severe patients. With the increased number of severe patients in the validation set, it now appears that this methodology should be utilized more frequently in our models. Another approach is to create separate models for severe and non-severe patients (the SPOC system has proven its ability to determine the difference). Of course, an important consideration is whether fixing the RDI of severe patients is even an important issue if this device is to be used only for "screening".

The second source of under prediction is the lack of accurate sleep scoring in the SPOC data. This issue is particularly relevant for SPOC-22 which is moderate and was our only diagnostic disagreement. The SPOC prediction of RDI was 7.2 whereas the PSG RDI was 21.5. However, patient 22 was awake for over half the night. During this waking period, the SPOC system predicted an RDI of close to zero causing the overall RDI to be artificially low. SPOC-22 was rather extreme in his wake time vs. sleep time, taking 86 minutes to fall asleep whereas the other patients averaged only 14 minutes to fall asleep. With a more appropriate estimate of sleep-time, the SPOC RDI prediction for patient 22 would have been 14, which would have been a diagnostic agreement. Improving sleep time estimates, if possible, would appear to be an effective means of improving the RDI prediction for mild and moderate patients.

Conclusion

This document has summarized the efforts and results obtained from this SPCDS project. The data driven approach has created a system that appears to be robust to differences in patient population and performs well relative to other systems on the market. The system uses a unique combination of nasal pressure, saturation, and plethysmography parameters and each of the 4 parameters contributes unique information that is utilized by the system. Although there were a few outliers in the validation set that produced a lower than expected correlation with RDI, these outliers are largely caused by two factors: (1) the difference between sleep time and valid data time (our surrogate for sleep), and (2) our focus on correctly discriminating mild and moderate patients. The largest outliers were limited to the very high RDI patients (RDI>80) and the RDI correlation for patients with RDI<80 was 0.96. Even with the sleep-time induced underestimates, the White/Westbrook diagnostic agreement was 93%. With compensation for this sleep time disparity, the diagnostic agreement was 100%.

In the near future, we propose to continue development of the algorithms and primarily focus on three issues:

1. Detection of sleep and awake time
2. Detection of central vs. obstructive apnea
3. Use of dual (mild vs. severe) models or more complex models with the larger training and validation sets.

Example 11

Warfighter Autonomous or Remotely Controlled Advanced Resuscitation Ensemble (WARCARE)—Enroute Trauma and Resuscitative Care, Expeditionary Logistics and Expeditionary Casualty Care The technical objectives according to this invention are to integrate disruptive non-invasive monitoring (photoplethysmography [PPG] derived parameters) and therapeutic (intranasal drug delivery system) technologies that collect data from and deliver medication to a unique anatomical site (nasal alae—lateral fleshy portions of the nostrils) which allows a reduced footprint and power requirements in order to automate life support in austere environments. Specifically, this invention provides technologies and methods/algorithms to 1) detect impending hypovolemic shock (IHS) and commence resuscitation when IHS is detected and 2) provide opioid pain control and monitor its effectiveness with or without vascular access and with minimal AFMSA personnel support by providing a unique "Monitoring and Resuscitation from a Single Point of Contact" (MR SPOC) sensor array at the nasal alae (a site which allows: markedly improved and unique [cerebral blood flow surrogate and venous capacitance measurements] physiologic data due to improved signal to noise ratios; increased light transmission with less tissue scatter which reduces power requirements; and a unique vascular supply devoid of sympathetic innervations which provides robust data even in the presence of peripheral "shutdown" from stress, anxiety and/or hypovolemia) and 3) integration of these technologies into existing life support equipment (e.g. LSTAT) where applicable to serve as a force multiplier across the AE continuum (Levels 1-5) while providing improved care for the warfighter. (A companion WP will address non-invasive detection of compartment syndrome, monitoring of cerebral perfusion and closed-loop mechanical ventilation) (4) Research Gaps to date (1) IHS is undiagnosable with equipment currently available to AFMSA personnel. Early recognition of IHS has been identified by DoD and DARPA as the most pressing issue in in-theater trauma care. Therapeutic treatment options for shock prior to institution of vascular access are lacking. Aside from tourniquets and direct pressure, military medicine lacks therapies to combat IHS prior to intravenous (IV) access. Early intervention to prevent shock reduces morbidity and mortality. 3) Technologies for early (Level 1) and continued (Levels 2-5) administration and optimal titration of opioids are unavailable. Recent studies indicate that early administration of opioids reduces the incidence of PTSD. Opioid administration in austere environments is prone to under- and overdosing. Underdosing predisposed to PTSD, overdosing can cause respiratory depression or arrest and hypotension, especially in face of hypovolemia. Warfighters deserve optimal pain control. 4) Software/hardware solutions for integration of novel and existing monitoring technologies to automate life support are unavailable. AFMSA personnel must evaluate data (e.g. cardiorespiratory and other physiologic parameters) from multiple sources and warfighters simultaneously leading to information overload and fatigue, especially in austere AE environments. Confirmation of hardware and software operation for data collection is performed, in a Clinical Research Center (CRC) (Study 1) using a tilt table to produce acute volume depletion to the head and one in women during Caesarean section (Study 2) to demonstrate the power of PPG to rapidly detect swings in intravascular volume. Tilt tables are a well-recognized technique for simulating acute hemorrhagic shock. Delivery by Caesarean section is accompanied by rapid and significant swings in intravascular volume due to fluid administration, spinal anesthesia, medication delivery, and delivery of the neonate and placenta. Monitoring PPG from the nasal ala as well as a peripheral site (e.g. fingers) and other parameters before, throughout and after the procedure demonstrates the specificity and sensitivity of the software algorithms in detecting volume changes.

Pharmacokinetic (PK) and pharmacodynamic (PD) effects of opioids, including intranasal delivery. Studies are conducted to confirm the ability of the present technology to monitor and control delivery of opioids, as follows: A first will determines the effects of IV opioid (fentanyl) administration on PK (Cmax, Tmax, and AUC) and PD (cardiorespiratory [CR] parameters including vital signs and PPG derived measurements [e.g. respiratory rate, effort and I:E ratio, cerebral perfusion, venous capacitance, and heart rate variability]) with and without supplemental oxygen. The purpose of this study is to study the effects of opioid delivery on the PPG and CR parameters to test robustness of algorithms for closed-loop delivery of opioids. A second study determines the PKs (e.g., Tmax, Cmax, AUC) of nasally administered fentanyl administration and compares them to the IV PK values obtained in the first study.

Data collected from these studies is integrated into existing algorithms to: 1) provide early detection of IHS and guide intranasal therapy with vasopressin until IV access and provide continued monitoring and guidance (whether by closed-loop control or advisory implementation). Advisory algorithms display suggested therapeutic interventions to AFMSA and/or other personnel for fluid therapy throughout the transport continuum (Levels 1-5), provides opioid therapy initially via the intranasal route and then IV (closed-loop or advisory) while monitoring for cardiorespiratory effects and 3) provides hardware/software solutions to integrate existing AFMSA monitoring and treatment capabilities into WARCARE.

How WARCARE Delivers Medications to Reduce the Incidence of PTSD in Warfighters

Intranasal medication delivery, including opioids, has been well studied and small devices similar to those proposed for use herein have been developed. Intranasal delivery allows for rapid absorption of medications, some of which are absorbed almost as rapidly as IV administration. Intranasal delivery provides high bioavailability (frequently up to 70% or greater of an IV injection) and the time to maximum concentration (Tmax) approaches that of IV injections (<5 min for some opioids).

In real-world practice, an injured warfighter who is conscious could rapidly place MR SPOC and WARCARE would immediately activate and begin providing pain and/or other medications based on data interpretation by algorithms and/or by on-site or remote medical personnel. If the injured warfighter is incapacitated, a fellow warfighter would place MR SPOC on him/her. Additionally, since each warfighter would carry the highly concentrated medications for WARCARE, these could be used on another wounded warfighter, thus increasing the amount of medication available in the field.

Other Features of WARCARE: Role of an Accelerometer

An additional feature, an accelerometer, monitors the warfighter. Since the accelerometer can detect body position it can be used to compensate for changes in the PPG signals based on the relative position of the nasal alae to the heart.

Likewise, an accelerometer detects very regular but intense body movement indicative of seizure activity, in which case a benzodiazepine or other antiseizure medications are delivered once MR SPOC is placed by a fellow combatant. In some instances, the accelerometer is the first indication of a problem with a warfighter, prior to the placement of MR SPOC.

Impact of WARCARE in the Military Environment: Force Multiplier

WARCARE provides both the initial (Level 1) monitoring and medication delivery and then continue to provide monitoring and control infusion pumps (e.g. a PCA pumps) once IV access is obtained. WARCARE is a force multiplier as it allows a limited number of skilled medical personnel to monitor and treat a large number of injured warfighters throughout their transport from Level I to Level V care. It is envisioned that the totally autonomous (closed-loop, servo-control) feature will only be activated during Level 1 care by Special Forces units that are self-reliant and may not have access to advanced medical support for extended periods of time.

Technical Rationale, Technical Approach, and Constructive Plan

Protean research efforts, including PPG monitoring from peripheral locations (predominantly the fingers), have failed to identify a noninvasive measurement or group of measurements that reliably predict IHS.

Likewise, efforts to identify a reliable means for the early administration of opioids for pain control at far forward locations to reduce the incidence of PTSD have largely failed.

When using raw PPG signals from the nasal alae and our algorithms (rather than the processed signals from a pulse oximeter) the amplitude of the PCC reflects cerebral blood flow. The absence of venous valves between the chest and head allows monitoring of venous capacitance and the signals reflect changes in intrathoracic pressure, thus allowing the monitoring and treatment of the warfighter using MR SPOC. Because this site has not been previously appreciated, the potential for providing both monitoring and medication delivery from a single site has not been considered. Further, with the unique extremity injuries due to IEDs, diagnosis, monitoring and treatment from the nasal alae makes infinite sense in the 21st century battlefield. To validate the hypothesis that diagnosis, monitoring and treatment can be effectively performed with MR SPOC, studies are conducted to confirm the sensitivity and specificity of PPG measurements to detect intravascular volume perturbations, to determine the PK (e.g., Cmax, time to maximum blood concentration; Tmax, time to Cmax; and AUC, area under the concentration-time relationship) and PD of IV opioid administration, particularly on brainstem effect sites (to determine what cardiorespiratory parameters need to be measured in order to provide safe opioid delivery under battlefield and transport conditions); and to confirm the PK (e.g., Tmax, Cmax, AUC) of nasally administered opioid administration and compare them to the IV PK.

A brief synopsis of the clinical studies is provided below:
1. Determine that Intravascular Volume Changes are Accurately Reflected with Nasal Alae Monitoring:

Delivery by Caesarean section is accompanied by significant swings in intravascular volume due to fluid administration, spinal anesthesia, medication delivery, and delivery of the neonate and placenta. Monitoring PPG and other parameters before, throughout and after the procedure demonstrates the specificity and sensitivity of the software algorithms in detecting volume changes.

a. With IRB approval, women scheduled for elective caesarean section are recruited (number required for statistical significance to be based on a power analysis after a pilot study).
b. Pulse oximeter sensors are placed on one nasal ala (Respironics "Y" sensor with earlobe clip), a finger and a toe. The sensors are connected to 3 identical OxyPleth pulse oximeters with signal averaging set at 2 sec. The oximeters are connected to a computer running proprietary software that separates the raw PPG signal into PCC and LFC components. Data is displayed and stored for analysis.
c. Signals for the Philips Intelliview™ monitor are used to monitor vital signs and are ported to the computer and the data stored for analysis.
d. A record of all interventions including drug and fluid administration is collected using the software running on the computer.
e. Baseline data (prior to placement of spinal anesthetic) is collected for a minimum of 5 min with subjects in a position of comfort and then continuously throughout the Caesarean section.
f. 500 mL of crystalloid is infused by standard protocol.
g. Spinal anesthesia using 1.5 mL of 0.75% bupivacaine is administered. This provides anesthesia as well as a sympathectomy to a mid to upper thoracic level which mimics acute blood loss and/or spinal cord injury.
h. Phenylephrine and/or ephedrine are usually administered at this time to attenuate the physiological effects of local anesthetic-induced sympathectomy.
i. The newborn is then delivered by Caesarean section. Fluid administration during this period is usually an additional 500 mL of crystalloid.
j. Blood loss during delivery and the immediate post-delivery period usually averages 800-1,000 mL.
k. Subjects are continuously monitored post-operatively as long as they remain in the operative suite.
l. Physiological data is analyzed by univariate and multivariate logistical regression, and by receiver operating characteristic (ROC) analysis.

2. Determine the Effects of IV Opioid (Fentanyl) Administration on PK (Cmax, Tmax, and AUC) and PD (Cardiorespiratory Parameters Including Vital Signs and PPG) with and without Supplemental Oxygen:
a. With IRB approval, healthy subjects who provide informed consent are recruited.
b. The study is performed in a general clinical research center (GCRC) over a 2 day period. Subjects are randomized to receive oxygen at 4 L/minute by face mask or not receive oxygen on one of the two days.
c. Subjects have an arterial catheter placed in a radial artery after an Allen test documents adequate collateral circulation. The arterial catheter monitors blood pressure and is used for blood samples to measure fentanyl concentrations in the blood and arterial blood gases, from which oxygen saturation is calculated.
d. An IV catheter is emplaced for infusion of fentanyl, and if necessary, fluid and other drugs (e.g., naloxone as rescue medication for fentanyl overdose). Different doses of fentanyl are administrated via an IV infusion every 60 min using an escalation protocol for a total of 5 study periods: 1) vehicle infusion (no fentanyl), 2) low dose, 3) moderate dose, 4) high dose, and 5) washout period (fentanyl infusion discontinued). Note: A board certified anaesthesiologist monitors the patient throughout this protocol, and has airway support equipment and naloxone available for rapid reversal.
e. Subjects are monitored with a 12-channel polysomography (PSG) system, the data from which is processed and analyzed.
f. Pulse oximeter sensors are placed on one nasal ala (Respironics "Y" sensor with earlobe clip), and a finger. The sensors are connected to 2 identical OxyPleth pulse oximeters with signal averaging set at 2 sec. The oximeters are connected to a computer running proprietary software that separates the raw PPG signal into PCC and LFC components. Data is displayed and stored for analysis.
g. End tidal carbon dioxide (PETCO2) is monitored using a nasal cannula either as part of the PSG system or with a stand-alone monitor (e.g. Oridion Capnostream® 20 monitor).
h. After all sensors are in place, baseline measurements are collected for at least 15 min, prior to initiation of the vehicle infusion.
i. Data from all sensors is collected for later analysis. The "gold standard" PD effect of fentanyl, the rise in arterial CO2 as measured by arterial blood gas analysis, is used.
j. At the end of study on day one, the subjects remain overnight in the GCRC with the radial artery catheter in place so that they can then complete the remaining limb of the study on Day 2.
k. Physiological data is analyzed by univariate and multivariate logistical regression to examine what physiological parameters (single or grouped) best predict the rise in arterial CO2 levels in the absence and presence of supplemental oxygen. In addition, the relations between fentanyl blood levels and key cardiorespiratory parameters are analyzed using repeated measures ANOVA.

3. Comparison of Intranasal and Intravenous Drug Delivery of Opioids (Fentanyl):
a. With IRB approval, healthy subjects who can provide informed consent are recruited.
b. PKs (e.g., Tmax, Cmax, AUC) of nasally administered fentanyl administration are obtained and compared to the IV PK values obtained in Study 2.
c. Nasal fentanyl is administered in the GCRC using different but complementary strategies: 1) mode of nasal delivery (aerosol or syringe), and 2) escalating doses (vehicle, low, moderate, high, washout) and type of delivery (single nasal bolus versus multiple small boluses).
d. To facilitate comparison of the PK of nasal and IV fentanyl administration, only standard routine monitoring is used. A board certified anesthesiologist is present during the course of this study.
e. Standard analyses is carried out to determine the effect of anatomical site (nasal versus IV), manner of nasal fentanyl administration (aerosol versus syringe), fentanyl dose, and the frequency of dosing with nasal administration on fentanyl PK.

The results of the first study are analyzed. It is anticipated that they confirm that SPOC is a sensitive and specific indicator of acute volume changes E. General Discussion of Other Research in this Area
1. Diagnosis of Impending Hypovolemic Shock:
There is a voluminous literature on the detection and treatment of hypovolemic shock. Despite this, finding a reliable noninvasive measurement or group of measurements that predict IHS remains elusive. For instance, in April, 2009 DARPA promulgated the solicitation "Continuous, Non-Invasive Monitoring of Blood Pressure—Request for Information (SN09-36)".

This led to a workshop where key stakeholders concluded that blood pressure is a late indicator of hypovolemic shock and could not reliably predict it. Likewise, with funding from TATRC (Telemedicine and Advanced Technology Research Center, Fort Detrick, Md.) researchers specifically explored whether PPG derived parameters (taken from a pulse oximeter and recorded from a digit) could predict major hemorrhage. They concluded that "Our multivariate analysis suggested that PPG respiration-induced waveform variation (RIWV) metrics may be independent predictors of major hemorrhage (P<0.01) above and beyond SBP, DBP, HR, RR, and SpO2, although the added benefit was incremental. Photoplethysmogram RIWV metrics could therefore be useful in conjunction with other vital signs for patient monitoring." (Chen L, et al. Is Respiration-Induced Variation in the Photoplethysmogram Associated with Major Hypovolemia in Patients with Acute Traumatic Injuries? Shock 2010; 34:455-460).

Beginning in 1987, a group of researchers in Israel conducted a series of studies that showed that variations in systolic blood pressure in mechanically ventilated animals and humans were predictive of volume status and could be used to guide volume replacement therapy. (Perel A, et al. Systolic Blood Pressure Variation is a Sensitive Indicator of Hypovolemia in Ventilated Dogs Subjected to Graded Hemorrhage. Anesthesiology 1987; 67:498-502; Perel A. Assessing Fluid Responsiveness by the Systolic Pressure Variation in Mechanically Ventilated Patients. Anesthesiology 1998; 89:1309-1310; Perel A. Automated Assessment of Fluid Responsiveness in Mechanically Ventilated Patients. Anesth Analg 2008; 106:1031-1033). These results have been validated worldwide. Subsequently, it was shown that PPG could also be used. (Pinsky M. At the Threshold of Noninvasive Hemodynamic Monitoring. Anesthesiology 2007; 106:1084-1085). Unfortunately, none of this research has led to a means to predict IHS in spontaneously breathing patients.

2. Intranasal Administration of Opioids to Control Pain and Reduce the Incidence of PTSD:

There is an extensive literature documenting the PK and PD of intranasally administered opioids (and other medications including ketamine and benzodiazepines). Several recent review articles provided detailed information. (Veldhorst-Janssen N M, et al. A review of the clinical pharmacokinetics of opioids, benzodiazepines, and antimigraine drugs delivered intranasally. Clin Ther. 2009; 31:2954-87; Fisher A, et al. Pharmacokinetic comparisons of three nasal fentanyl formulations; pectin, chitosan and chitosan-poloxamer 188. Int J Clin Pharmacol Ther. 2010; 48:138-145). A recent widely publicized article showed that the incidence of post-traumatic stress disorder (PTSD) was reduced from 76% to 61% if warfighters received morphine during early resuscitation following serious injuries. (Holbrook, T L, et al, Morphine Use after Combat Injury in Iraq and Post Traumatic Stress Disorder. N Engl J. Med. 2010; 14; 362: 110-117). Medications such as morphine and ketamine have been shown to impede memory consolidation, and as a result reduce the severity of the stress reaction to memories of trauma. (Mcghee, L. L, et al. The Correlation Between Ketamine and Posttraumatic Stress Disorder in Burned Service members. The Journal of Trauma Injury, Infection, and Critical Care: Volume 54 number 5). It has been postulated that a major cause of PTSD is the permanent distortion of endorphin responsiveness to stress. (Hyson, R. L. et al, Extent and control of shock affects naltrexone sensitivity of stress-induced analgesia and reactivity to morphine. Pharmacology and Biochemical Behavior 17: 1019-1025, 1982). It is believed that trauma causes the body to release endorphin levels high enough to produce a withdrawal-like syndrome which left untreated results in recollections of the traumatic event, recurrent dreams, and extreme psychological stress. (Wilson J. P. Assessing Psychological Trauma and PTSD Second edition: 7-45. Guilford Press, 2004) These episodes may be psychologically damaging and produce biological reactions, including a dysregulation of the stress response. (Feldner, M, et al, A Critical Analysis of Approaches to Targeted PTSD Prevention: Current Status and Theoretically Derived Future Directions. Behavior Modification Vol. 31 Num 1 20-116, 2007). Constant stimulation of opioid receptors may strengthen an opposing system with anti-opioid effects. Eventually, the opposing system dominates, and the patient experiences a general deficit of endorphin function.

What is claimed is:

1. A medication delivery control system comprising:
   (a) an apparatus comprising at least one photoplethysmography (PPG) sensor that obtains a PPG signal from a site at a subject's nose;
   (b) an infusion device that provides medication to the subject's nose;
   (c) a controller for receiving PPG signals from the PPG sensor and, based on the signals, increasing, decreasing or maintaining a rate of infusion of the infusion device, and
   (d) an accelerometer or other motion sensing device
   wherein the system is in a sleep mode wherein power consumption is reduced until the controller determines that the subject is sleeping or in state of respiratory depression based on signals from the accelerometer or other motion sensing device; and
   wherein the medication delivery control system is a wearable device adapted to be secured to the nose and/or head of the subject.

2. The medication delivery control system according to claim 1, wherein the PPG signals are obtained from the subject's nasal alar.

3. The medication delivery control system according to claim 1, further comprising a nasal pressure or flow sensor, and optionally, an ECG electrode.

4. The medication delivery control system according to claim 1, further comprising an intranasal tube that is adapted to be emplaced inside the subject's nostril and delivers pre-metered doses of medications.

5. The medication delivery control system according to claim 4, wherein the system delivers nitric oxide, histamine, or methacholine to nasal mucosa, either as part of the medications or as a separate feed.

6. The medication delivery control system of claim 4, wherein the medications comprise at least one of opioids, opioid antagonists, vasoactive drugs, steroids, dissociative agents and anxiolytics.

7. The medication delivery control system of claim 4, wherein the system delivers medications through the nasal epithelium.

8. The medication delivery control system of claim 1, further comprising at least one PPG sensor adapted to be secured to a peripheral site of the subject.

9. The medication delivery control system of claim 1, wherein the system:
   (i) obtains measurements of at least one of the subject's vital signs selected from the group consisting of nasal pressure/flow, electrocardiographic signals, blood pressure, heart rate, heart rate variability, arrhythmias, respiratory rate, respiratory effort indicative of work of breathing, inspiratory and expiratory breathing ratios (I:E ratios), patterns of indicative of normal respiration or respiratory depression, plethysmography signals, blood oxygen saturation, blood volume, including local arterial blood flow amplitude, venous capacitance and comparative flows and capacitance from two or more site indicative of hypovolemia/shock and/or loss of extremity perfusion, pulse transit time, pulse wave velocity and combinations thereof, (ii) processes the measurements to determine a relative state of health and, based on the determination, (iii) infuses at least one medication to the subject based on the determination in (ii).

10. The medication delivery control system of claim 1, wherein the system is operated by remote personnel.

11. The medication delivery control system of claim 1, wherein the system is part of a helmet, telemetry or communications gear.

12. The medication delivery control system of claim 9, wherein the system wirelessly communicates vital sign information to remote personnel.

\* \* \* \* \*

UNITED STATES PATENT AND TRADEMARK OFFICE
CERTIFICATE OF CORRECTION

PATENT NO. : 9,950,112 B2
APPLICATION NO. : 13/817165
DATED : April 24, 2018
INVENTOR(S) : Melker et al.

It is certified that error appears in the above-identified patent and that said Letters Patent is hereby corrected as shown below:

On the Title Page

Item (75) should read:
Richard J. Melker, Gainesville, FL (US);
Donn M. Dennis, Gainesville, FL (US);
Jeremy Melker, Gainesville, FL (US);
Mark Rice, Jacksonville, FL (US);
Robert Hurley, Gainesville, FL (US);
Mark Gold, Ponte Vedra Beach, FL (US)

Signed and Sealed this
Sixteenth Day of April, 2019

Andrei Iancu
*Director of the United States Patent and Trademark Office*